(12) United States Patent
Kawazoe et al.

(10) Patent No.: US 7,807,856 B2
(45) Date of Patent: Oct. 5, 2010

(54) PROCESS FOR PRODUCTION OF 2-BENZYLPHENOL COMPOUND

(75) Inventors: Kentaro Kawazoe, Shizuoka (JP); Yasuo Yoshida, Shizuoka (JP)

(73) Assignee: Ihara Chemical Industry Co., Ltd., Tokyo (JP)

( * ) Notice: Subject to any disclaimer, the term of this patent is extended or adjusted under 35 U.S.C. 154(b) by 357 days.

(21) Appl. No.: 11/667,461

(22) PCT Filed: Nov. 7, 2005

(86) PCT No.: PCT/JP2005/020349
§ 371 (c)(1),
(2), (4) Date: Oct. 2, 2007

(87) PCT Pub. No.: WO2006/051747
PCT Pub. Date: May 18, 2006

(65) Prior Publication Data
US 2008/0194882 A1 Aug. 14, 2008

(30) Foreign Application Priority Data
Nov. 10, 2004 (JP) .............................. 2004-326161
Aug. 10, 2005 (JP) .............................. 2005-231714

(51) Int. Cl.
*C07C 37/07* (2006.01)
(52) U.S. Cl. ..................... 568/809; 568/814
(58) Field of Classification Search ................... 568/809
See application file for complete search history.

(56) References Cited

U.S. PATENT DOCUMENTS

| 3,247,278 | A | * | 4/1966 | Garwood et al. ............ 423/443 |
| 5,072,017 | A | | 12/1991 | Buysch et al. ............... 558/376 |
| 5,741,937 | A | | 4/1998 | Muller et al. ................ 568/312 |

FOREIGN PATENT DOCUMENTS

| GB | 1258554 | 12/1971 |
| JP | 1-193234 | 8/1989 |

OTHER PUBLICATIONS

Fronza et al., 36 Tetra. Lett., 122-24 (1995).*
Zhao et al., 38 Pharm. Chem. J., 229-38 (2004).*
Du Feu et al., J. Chem. Soc., 53-60 (1397).*
Kock et al., 35 Tetra. Lett., 1137-1140 (1994).*
Batt et al., Journal of Medicinal Chemistry (1990), 33(1), p. 360-370.*
Aizenshtat, Z. et al., 'Chlorocarbonylbis (triphenylphosphine) iridium-Catalyzed Isomerization, Isoaromatization, and Disproportionation of Some Cycloalkanones Having Exocyclic Double Boncs', J. Org. Chem., 1977, vol. 42, No. 14, pp. 2386-2394.
Horning, E.C., 'Alicyclic-Aromatic Isomerizations. Catalytic Isomerization of 2, 6-Dibenzalcyclohexanone and Carvone', J. Org. Chem., 1945, vol. 10, pp. 263-266.
Pickholtz, Y. et al., 'Homogeneous Isoaromatization of Alicyclic Dieones Catalyzed by Complexes of the Platinum Group', Tetrahedron Letters, 1974, No. 14, pp. 1263-1266.

* cited by examiner

*Primary Examiner*—Brian J Davis
(74) *Attorney, Agent, or Firm*—Bacon & Thomas, PLLC

(57) ABSTRACT

A process for producing a 2-benzylphenol compound represented by the following formula (2):

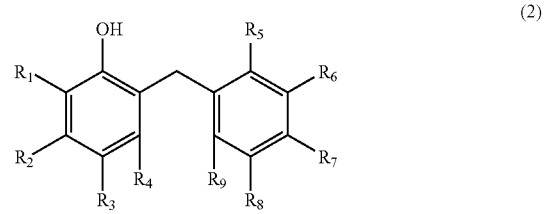

(2)

wherein, $R_1$, $R_2$, $R_3$ and $R_4$ may be the same or different and are each independently hydrogen atom, alkyl group or the like; and $R_5$, $R_6$, $R_7$, $R_8$ and $R_9$ are the same or different and are each independently hydrogen atom, alkyl group or the like, the process including reacting, in the presence of a dehydrogenating agent, a benzylidenecyclohexanone compound represented by the following formula (1):

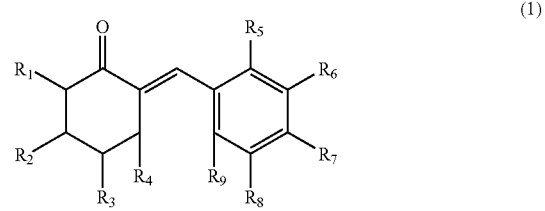

(1)

wherein, $R_1$, $R_2$, $R_3$, $R_4$, $R_5$, $R_6$, $R_7$, $R_8$ and $R_9$ have the same definitions as given above.

20 Claims, No Drawings

PROCESS FOR PRODUCTION OF 2-BENZYLPHENOL COMPOUND

TECHNICAL FIELD

The present invention relates to a process for producing a 2-benzylphenol compound substantially free from isomers, efficiently and selectively.

BACKGROUND ART

For production of 2-benzylphenol compound, there has been known, for example, a process which comprises subjecting 2-benzyloxyphenyl magnesium bromide and a benzaldehyde to a condensation reaction and then subjecting the reaction product to catalytic reduction to give rise to deprotection and dehydroxylation simultaneously (reference is made to Patent Literatures 1 and 2). In this process, however, it is essential to bond a protecting group to 2-bromophenol used as a raw material, then conduct a Grignard reaction, thereafter conduct deprotection; therefore, there have been various problems, for example, the steps are many and the operation is complicated, the use of metallic magnesium (which is unstable in the air) makes difficult the handling, the catalytic reduction requires a special high-pressure reactor in many cases, various counter-measures for safety need be taken in each step, and isomers are formed in some cases.

Patent Literature 1: JP-A-2001-08239
Patent Literature 2: WO 02/28872

DISCLOSURE OF THE INVENTION

Task to be Achieved by the Invention

There has been desired a novel process for production of 2-benzylphenol compound, which is free from the above-mentioned drawbacks of the prior art and can produce a 2-benzylphenol compound easily, efficiently and selectively.

Means for Achieving the Task

In view of the above situation, the present inventor made a study on a process for producing a 2-benzylphenol compound easily, efficiently and selectively. As a result, it was found unexpectedly that the above task can be achieved by reacting a benzylidenecyclohexanone compound (which is easily obtained by subjecting, to a condensation reaction, a cyclohexanone compound and a benzaldehyde compound) in the presence of a dehydrogenating agent (e.g. a palladium catalyst or sulfur) and thereby a 2-benzylphenol compound substantially free from isomers can be produced efficiently and selectively. The finding has led to the completion of the present invention.

EFFECT OF THE INVENTION

The present invention provides a process for producing a 2-benzylphenol compound substantially free from isomers, efficiently and selectively. According to the present process, a raw material, benzylidenecyclohexanone compound (which is easily obtained, for example, by condensation of a cyclohexanone compound and a benzaldehyde compound in the presence of a base) is reacted in the presence of a dehydrogenating agent (e.g. a palladium catalyst or sulfur), whereby an intended 2-benzylphenol compound can be produced at a high selectivity, efficiently and in an simple operation, under mild conditions without using any special reactor.

BEST MODE FOR CARRYING OUT THE INVENTION

The present invention is described in detail below.
The present invention has achieved the above task by providing the following inventions [1] to [16].

[1] A process for producing a 2-benzylphenol compound represented by the following general formula (2)

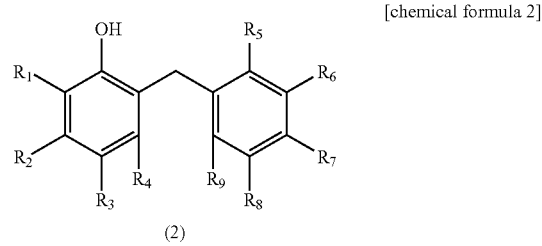

[chemical formula 2]

(2)

(in the formula, $R_1$, $R_2$, $R_3$ and $R_4$ may be the same or different and are each independently hydrogen atom, substituted or unsubstituted alkyl group, substituted or unsubstituted cyclic alkyl group, trialkylsilyl group, alkoxy group, trialkylsilyloxy group, hydroxyalkyl group, alkoxyalkyl group, carboxyl group or metal salt thereof, alkoxycarbonyl group, amino group, alkylamino group, alkylcarbonylamino group, nitro group, substituted or unsubstituted phenyl group, substituted or unsubstituted phenoxy group, or substituted or unsubstituted heteroaryl group; two of $R_1$, $R_2$, $R_3$ and $R_4$ may be bonded with each other to form a ring; $R_5$, $R_6$, $R_7$, $R_8$ and $R_9$ may be the same or different and are each independently hydrogen atom, substituted or unsubstituted alkyl group, substituted or unsubstituted cyclic alkyl group, substituted or unsubstituted alkenyl group, substituted or unsubstituted cyclic alkenyl group, alkynyl group, substituted or unsubstituted cyclic alkynyl group, trialkylsilyl group, hydroxyl group, alkoxy group, trialkylsilyloxy group, hydroxyalkyl group, alkoxyalkyl group, carboxyl group or metal salt thereof, alkoxycarbonyl group, amino group, alkylamino group, alkylcarbonylamino group, halogen atom, nitro group, substituted or unsubstituted phenyl group, substituted or unsubstituted phenoxy group, or substituted or unsubstituted heteroaryl group; two of $R_5$, $R_6$, $R_7$, $R_8$ and $R_9$ may be bonded with each other to form a ring), characterized by reacting, in the presence of a dehydrogenating agent, a benzylidenecyclohexanone compound represented by the following general formula (1)

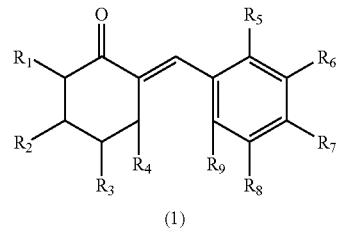

[chemical formula 1]

(1)

(in the formula, $R_1$, $R_2$, $R_3$, $R_4$, $R_5$, $R_6$, $R_7$, $R_8$ and $R_9$ have the same definitions as given above).

[2] A process for producing a 2-benzylphenol compound represented by the following general formula (2)

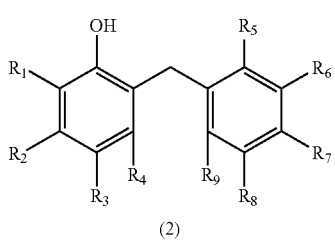

(2)

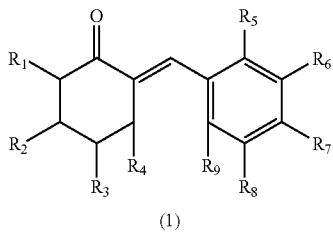

(1)

(in the formula, $R_1$, $R_2$, $R_3$ and $R_4$ may be the same or different and are each independently hydrogen atom, substituted or unsubstituted alkyl group, substituted or unsubstituted cyclic alkyl group, trialkylsilyl group, alkoxy group, trialkylsilyloxy group, hydroxyalkyl group, alkoxyalkyl group, carboxyl group or metal salt thereof, alkoxycarbonyl group, amino group, alkylamino group, alkylcarbonylamino group, nitro group, substituted or unsubstituted phenyl group, substituted or unsubstituted phenoxy group, or substituted or unsubstituted heteroaryl group; two of $R_1$, $R_2$, $R_3$ and $R_4$ may be bonded with each other to form a ring; $R_5$, $R_6$, $R_7$, $R_8$ and $R_9$ may be the same or different and are each independently hydrogen atom, substituted or unsubstituted alkyl group, substituted or unsubstituted cyclic alkyl group, substituted or unsubstituted alkenyl group, substituted or unsubstituted cyclic alkenyl group, substituted or unsubstituted alkynyl group, cyclic alkynyl group, trialkylsilyl group, hydroxyl group, alkoxy group, trialkylsilyloxy group, hydroxyalkyl group, alkoxyalkyl group, carboxyl group or metal salt thereof, alkoxycarbonyl group, amino group, alkylamino group, alkylcarbonylamino group, halogen atom, nitro group, substituted or unsubstituted phenyl group, substituted or unsubstituted phenoxy group, or substituted or unsubstituted heteroaryl group; two of $R_5$, $R_6$, $R_7$, $R_8$ and $R_9$ may be bonded with each other to form a ring), characterized by subjecting, to a condensation reaction in the presence of a base, a cyclohexanone compound represented by the following general formula (3)

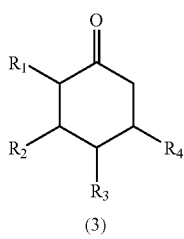

(3)

(in the formula, $R_1$, $R_2$, $R_3$ and $R_4$ have the same definitions as given above) and a benzaldehyde compound represented by the following general formula (4)

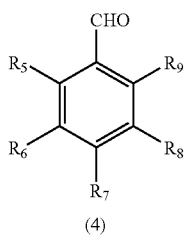

(4)

(in the formula, $R_5$, $R_6$, $R_7$, $R_8$ and $R_9$ have the same definitions as given above) to obtain a benzylidenecyclohexanone compound represented by the following general formula (1)

(in the formula, $R_1$, $R_2$, $R_3$, $R_4$, $R_5$, $R_6$, $R_7$, $R_8$ and $R_9$ have the same definitions as given above), and then reacting the benzylidenecyclohexanone compound in the presence of a dehydrogenating agent.

[3] A process for producing a 2-benzylphenol compound according to [1] or [2], wherein the dehydrogenating agent is a palladium catalyst or sulfur.

[4] A process for producing a 2-benzylphenol compound according to [1] or [2], wherein the dehydrogenating agent is a palladium catalyst.

[5] A process for producing a 2-benzylphenol compound according to [1] or [2], wherein the dehydrogenating agent is a heterogeneous palladium catalyst loaded on at least one kind of carrier selected from carbon, alumina, barium sulfate and calcium carbonate.

[6] A process for producing a 2-benzylphenol compound according to [1] or [2], wherein the dehydrogenating agent is palladium carbon.

[7] A process for producing a 2-benzylphenol compound according to any of [1] to [6], wherein the reaction of the benzylidenecyclohexanone compound represented by the general formula (1) is conducted in a temperature range of 150 to 280° C.

[8] A process for producing a 2-benzylphenol compound according to any of [1] to [7], wherein the reaction of the benzylidenecyclohexanone compound represented by the general formula (1) is conducted in the presence of a hydrogen acceptor.

[9] A process for producing a 2-benzylphenol compound according to any of [1] to [7], wherein the reaction of the benzylidenecyclohexanone compound represented by the general formula (1) is conducted in the presence of an olefin.

[10] A process for producing a 2-benzylphenol compound according to [8] or [9], wherein the reaction of the benzylidenecyclohexanone compound represented by the general formula (1) is conducted in a temperature range of 150 to 230° C.

[11] A process for producing a 2-benzylphenol compound according to [8] or [9], wherein the reaction of the benzylidenecyclohexanone compound represented by the general formula (1) is conducted in a temperature range of 150 to 200° C.

[12] A process for producing a 2-benzylphenol compound according to [1] or [2], wherein the dehydrogenating agent is sulfur.

[13] A process for producing a 2-benzylphenol compound according to any of [1], [2] and [12], wherein the reaction of the benzylidenecyclohexanone compound represented by the general formula (1) is conducted in a temperature range of 180 to 250° C.

[14] A process for producing a 2-benzylphenol compound according to any of [1] to [13], wherein the benzylidenecyclohexanone compound represented by the general formula (1) is 2-benzylidenecyclohexanone, 2-(4-methylbenzylidene)cyclohexanone, 2-(4-methoxybenzylidene)cyclohexanone, 2-(4-chlorobenzylidene)cyclohexanone, 2-(4-fluorobenzylidene)cyclohexanone, 2-(4-methylbenzylidene)-4-methylcyclohexanone, 2-(4-methoxybenzylidene)-4-methylcyclohexanone, 2-(4-chlorobenzylidene)-4-methylcyclohexanone, 2-(4-fluorobenzylidene)-4-methylcyclohexanone, 2-(4-methylbenzylidene)-4-chlorocyclohexanone, 2-(4-methoxybenzylidene)-4-chlorocyclohexanone, 2-(4-chlorobenzylidene)-4-chlorocyclohexanone, 2-(4-fluorobenzylidene)-4-chlorocyclohexanone, 2-(4-methylbenzylidene)-4-fluorocyclohexanone, 2-(4-methoxybenzylidene)-4-fluorocyclo-hexanone, 2-(4-chlorobenzylidene)-4-fluorocyclohexanone or 2-(4-fluorobenzylidene)-4-fluoromethylcyclohexanone.

[15] A process for producing a 2-benzylphenol compound according to any of [2] to [13], wherein the cyclohexanone compound represented by the general formula (3) is cyclohexanone or 4-methylcyclohexanone.

[16] A process for producing a 2-benzylphenol compound according to any of [2] to [15], wherein the benzaldehyde compound represented by the general formula (4) is benzaldehyde, 4-methylbenzaldehyde, 4-methoxybenzaldehyde, 4-chlorobenzaldehyde or 4-fluorobenzaldehyde.

The present invention is described in detail below.

The present process lies in a process for producing a 2-benzylphenol compound represented by the general formula (2), characterized by reacting a benzylidenecyclohexanone compound represented by the general formula (1) in the presence of a dehydrogenating agent.

Description is made first on the benzylidenecyclohexanone compound represented by the general formula (1), used as a raw material in the present process.

The $R_1$, $R_2$, $R_3$ and $R_4$ of the general formula (1) may be the same or different from each other and are each independently hydrogen atom; straight chain or branched chain C1 to C6 alkyl group (hereinafter, carbon atoms, for example, 1 to 6 carbon atoms are abbreviated to "C1 to C6), such as methyl group, ethyl group, n-propyl group, isopropyl group, n-butyl group, sec-butyl group, tert-butyl group, n-pentyl group, n-hexyl group or the like [the alkyl group may have substituents such as cyclic C3 to C6 alkyl group (e.g. cyclopropyl group, cyclobutyl group, cyclopentyl group or cyclohexyl group), tri(straight chain or branched chain C1 to C6 alkyl) silyl group (e.g. trimethylsilyl group or tert-butyldimethylsilyl group), straight chain or branched chain C1 to C6 alkoxy group (e.g. methoxy group, ethoxy group, n-propoxy group or isopropoxy group), tri(straight chain or branched chain C1 to C6 alkyl)silyloxy group (e.g. trimethylsilyloxy group or tert-butyldimethylsilyloxy group), straight chain or branched chain C1 to C6 hydroxyalkyl group (e.g. hydroxymethyl group or hydroxyethyl group), straight chain or branched chain (C1 to C6 alkoxy)-(C1 to C6 alkyl) group (e.g. methoxymethyl group, methoxyethyl group or ethoxyethyl group), straight chain or branched C1 to C6 haloalkyl group (e.g. fluoromethyl group, difluoromethyl group or trifluoromethyl group), nitro group, phenyl group, phenoxy group, hetero-aryl group (e.g. pyridyl group, thienyl group or furanyl group), and the like]; cyclic C3 to C6 alkyl group such as cyclopropyl group, cyclobutyl group, cyclopentyl group, cyclohexyl group or the like [the cyclic alkyl group may have substituents such as straight chain or branched chain C1 to C6 alkyl group (e.g. methyl group, ethyl group, n-propyl group, isopropyl group, n-butyl group, sec-butyl group, tert-butyl group, n-pentyl group or n-hexyl group), cyclic C3 to C6 alkyl group (e.g. cyclopropyl group, cyclobutyl group, cyclopentyl group or cyclohexyl group), tri(straight chain or branched chain C1 to C6 alkyl)silyl group (e.g. trimethylsilyl group or tert-butyldimethylsilyl group), straight chain or branched chain C1 to C6 alkoxy group (e.g. methoxy group, ethoxy group, n-propoxy group or isopropoxy group), tri(straight chain or branched chain C1 to C6 alkyl)silyloxy group (e.g. trimethylsilyloxy group or tert-butyldimethylsilyloxy group), straight chain or branched chain C1 to C6 hydroxyalkyl group (e.g. hydroxymethyl group or hydroxyethyl group), straight chain or branched chain (C1 to C6 alkoxy)-(C1 to C6 alkyl) group (e.g. methoxymethyl group, methoxyethyl group or ethoxyethyl group), straight chain or branched C1 to C6 haloalkyl group (e.g. fluoromethyl group, difluoromethyl group or trifluoromethyl group), nitro group, phenyl group, phenoxy group, hetero-aryl group (e.g. pyridyl group, thienyl group or furanyl group), and the like]; tri(straight chain or branched chain C1 to C6 alkyl)silyl group (e.g. trimethylsilyl group or tert-butyldimethylsilyl group); straight chain or branched chain C1 to C6 alkoxy group (e.g. methoxy group, ethoxy group, n-propoxy group or isopropoxy group); tri(straight chain or branched chain C1 to C6 alkyl)silyloxy group (e.g. trimethylsilyloxy group or tert-butyldimethylsilyloxy group); straight chain or branched chain C1 to C6 hydroxyalkyl group (e.g. hydroxymethyl group or hydroxyethyl group); straight chain or branched chain (C1 to C6 alkoxy)-(C1 to C6 alkyl) group (e.g. methoxymethyl group, methoxyethyl group or ethoxyethyl group); carboxyl group or metal salt thereof; (C1 to C6 alkoxy having the above meaning)carbonyl group; amino group; (C1 to C6 alkyl having the above meaning)amino group; (C1 to C6 alkyl having the above meaning)carbonylamino group; nitro group; phenyl group [the phenyl group may have substituents such as straight chain or branched chain C1 to C6 alkyl group (e.g. methyl group, ethyl group, n-propyl group, isopropyl group, n-butyl group, sec-butyl group, tert-butyl group, n-pentyl group or n-hexyl group), cyclic C3 to C6 alkyl group (e.g. cyclopropyl group, cyclobutyl group, cyclopentyl group or cyclohexyl group), tri(straight chain or branched chain C1 to C6 alkyl)silyl group (e.g. trimethylsilyl group or tert-butyldimethylsilyl group), hydroxyl group, straight chain or branched chain C1 to C6 alkoxy group (e.g. methoxy group, ethoxy group, n-propoxy group or isopropoxy group), tri(straight chain or branched chain C1 to C6 alkyl)silyloxy group (e.g. trimethylsilyloxy group or tert-butyldimethylsilyloxy group), straight chain or branched chain C1 to C6 hydroxyalkyl group (e.g. hydroxymethyl group or hydroxyethyl group), straight chain or branched chain (C1 to C6 alkoxy)-(C1 to C6 alkyl) group (e.g. methoxymethyl group, methoxyethyl group or ethoxyethyl group), halogen atom, nitro group, phenyl group, phenoxy group, hetero-aryl group (e.g. pyridyl group, thienyl group or furanyl group), and the like]; phenoxy group [the phenoxy group may have substituents such as straight chain or branched chain C1 to C6 alkyl group (e.g. methyl group, ethyl group, n-propyl group, isopropyl group, n-butyl group, sec-butyl group, tert-butyl group, n-pentyl group or n-hexyl group), cyclic C3 to C6 alkyl group (e.g. cyclopropyl group, cyclobutyl group, cyclopentyl group or cyclohexyl group), tri(straight chain or branched chain C1 to C6 alkyl)silyl group (e.g. trimethylsilyl group or tert-butyldimethylsilyl group), hydroxyl group, straight chain or branched chain C1 to C6 alkoxy group (e.g. methoxy group, ethoxy group, n-propoxy group or isopropoxy group), tri(straight chain or branched chain C1 to C6 alkyl)silyloxy group (e.g. trimethylsilyloxy group or tert-butyldimethylsilyloxy group), straight chain or branched chain C1 to C6 hydroxyalkyl group (e.g.

hydroxymethyl group or hydroxyethyl group), straight chain or branched chain (C1 to C6 alkoxy)-(C1 to C6 alkyl) group (e.g. methoxymethyl group, methoxyethyl group or ethoxyethyl group), halogen atom, nitro group, phenyl group, phenoxy group, hetero-aryl group (e.g. pyridyl group, thienyl group or furanyl group), and the like]; or hetero-aryl group (e.g. pyridyl group, thienyl group or furanyl group) [the hetero-aryl group may have substituents such as straight chain or branched chain C1 to C6 alkyl group (e.g. methyl group, ethyl group, n-propyl group, isopropyl group, n-butyl group, sec-butyl group, tert-butyl group, n-pentyl group or n-hexyl group), cyclic C3 to C6 alkyl group (e.g. cyclopropyl group, cyclobutyl group, cyclopentyl group or cyclohexyl group), tri(straight chain or branched chain C1 to C6 alkyl)silyl group (e.g. trimethylsilyl group or tert-butyldimethylsilyl group), hydroxyl group, straight chain or branched chain C1 to C6 alkoxy group (e.g. methoxy group, ethoxy group, n-propoxy group or isopropoxy group), tri(straight chain or branched chain C1 to C6 alkyl)silyloxy group (e.g. trimethylsilyloxy group or tert-butyldimethylsilyloxy group), straight chain or branched chain C1 to C6 hydroxyalkyl group (e.g. hydroxymethyl group or hydroxyethyl group), straight chain or branched chain (C1 to C6 alkoxy)-(C1 to C6 alkyl) group (e.g. methoxymethyl group, methoxyethyl group or ethoxyethyl group), halogen atom, nitro group, phenyl group, phenoxy group, hetero-aryl group (e.g. pyridyl group, thienyl group or furanyl group), and the like]. Two of $R_1$, $R_2$, $R_3$ and $R_4$ may be bonded with each other to form a ring.

The $R_5$, $R_6$, $R_7$, $R_8$ and $R_9$ of the general formula (1) may be the same or different from each other and are each independently hydrogen atom; straight chain or branched chain C1 to C6 alkyl group such as methyl group, ethyl group, n-propyl group, isopropyl group, n-butyl group, sec-butyl group, tert-butyl group, n-pentyl group, n-hexyl group or the like [the alkyl group may have substituents such as cyclic C3 to C6 alkyl group (e.g. cyclopropyl group, cyclobutyl group, cyclopentyl group or cyclohexyl group), tri(straight chain or branched chain C1 to C6 alkyl)silyl group (e.g. trimethylsilyl group or tert-butyldimethylsilyl group), straight chain or branched chain C1 to C6 alkoxy group (e.g. methoxy group, ethoxy group, n-propoxy group or isopropoxy group), tri(straight chain or branched chain C1 to C6 alkyl)silyloxy group (e.g. trimethylsilyloxy group or tert-butyldimethylsilyloxy group), straight chain or branched chain C1 to C6 hydroxyalkyl group (e.g. hydroxymethyl group or hydroxyethyl group), straight chain or branched chain (C1 to C6 alkoxy)-(C1 to C6 alkyl) group (e.g. methoxymethyl group, methoxyethyl group or ethoxyethyl group), straight chain or branched C1 to C6 haloalkyl group (e.g. fluoromethyl group, difluoromethyl group or trifluoromethyl group), nitro group, phenyl group, phenoxy group, hetero-aryl group (e.g. pyridyl group, thienyl group or furanyl group), and the like]; cyclic C3 to C6 alkyl group such as cyclopropyl group, cyclobutyl group, cyclopentyl group, cyclohexyl group or the like [the cyclic alkyl group may have substituents such as straight chain or branched chain C1 to C6 alkyl group (e.g. methyl group, ethyl group, n-propyl group, isopropyl group, n-butyl group, sec-butyl group, tert-butyl group, n-pentyl group or n-hexyl group), cyclic C3 to C6 alkyl group (e.g. cyclopropyl group, cyclobutyl group, cyclopentyl group or cyclohexyl group), tri(straight chain or branched chain C1 to C6 alkyl) silyl group (e.g. trimethylsilyl group or tert-butyldimethylsilyl group), straight chain or branched chain C1 to C6 alkoxy group (e.g. methoxy group, ethoxy group, n-propoxy group or isopropoxy group), tri(straight chain or branched chain C1 to C6 alkyl)silyloxy group (e.g. trimethylsilyloxy group or tert-butyldimethylsilyloxy group), straight chain or branched chain C1 to C6 hydroxyalkyl group (e.g. hydroxymethyl group or hydroxyethyl group), straight chain or branched chain (C1 to C6 alkoxy)-(C1 to C6 alkyl) group (e.g. methoxymethyl group, methoxyethyl group or ethoxyethyl group), straight chain or branched chain C1 to C6 haloalkyl group (e.g. fluoromethyl group, difluoromethyl group or trifluoromethyl group), nitro group, phenyl group, phenoxy group, hetero-aryl group (e.g. pyridyl group, thienyl group or furanyl group), and the like]; straight chain or branched chain C2 to C6 alkenyl group such as vinyl group, 1-propenyl group, 2-propenyl group or the like [the alkenyl group may have substituents such as cyclic C3 to C6 alkyl group (e.g. cyclopropyl group, cyclobutyl group, cyclopentyl group or cyclohexyl group), tri(straight chain or branched chain C1 to C6 alkyl)silyl group (e.g. trimethylsilyl group or tert-butyldimethylsilyl group), straight chain or branched chain C1 to C6 alkoxy group (e.g. methoxy group, ethoxy group, n-propoxy group or isopropoxy group), tri(straight chain or branched chain C1 to C6 alkyl)silyloxy group (e.g. trimethylsilyloxy group or tert-butyldimethylsilyloxy group), straight chain or branched chain C1 to C6 hydroxyalkyl group (e.g. hydroxymethyl group or hydroxyethyl group), straight chain or branched chain (C1 to C6 alkoxy)-(C1 to C6 alkyl) group (e.g. methoxymethyl group, methoxyethyl group or ethoxyethyl group), straight chain or branched chain C1 to C6 haloalkyl group (e.g. fluoromethyl group, difluoromethyl group or trifluoromethyl group), nitro group, phenyl group, phenoxy group, hetero-aryl group (e.g. pyridyl group, thienyl group or furanyl group), and the like]; straight chain or branched chain C2 to C6 alkynyl group such as ethynyl group, 1-propynyl group, 2-propynyl group or the like [the alkynyl group may have substituents such as cyclic C3 to C6 alkyl group (e.g. cyclopropyl group, cyclobutyl group, cyclopentyl group or cyclohexyl group), tri(straight chain or branched chain C1 to C6 alkyl)silyl group (e.g. trimethylsilyl group or tert-butyldimethylsilyl group), straight chain or branched chain C1 to C6 alkoxy group (e.g. methoxy group, ethoxy group, n-propoxy group or isopropoxy group), tri(straight chain or branched chain C1 to C6 alkyl)silyloxy group (e.g. trimethylsilyloxy group or tert-butyldimethylsilyloxy group), straight chain or branched chain C1 to C6 hydroxyalkyl group (e.g. hydroxymethyl group or hydroxyethyl group), straight chain or branched chain (C1 to C6 alkoxy)-(C1 to C6 alkyl) group (e.g. methoxymethyl group, methoxyethyl group or ethoxyethyl group), straight chain or branched chain C1 to C6 haloalkyl group (e.g. fluoromethyl group, difluoromethyl group or trifluoromethyl group), nitro group, phenyl group, phenoxy group, hetero-aryl group (e.g. pyridyl group, thienyl group or furanyl group), and the like]; cyclic C3 to C6 alkenyl group such as cyclopropenyl group, 1-cyclobutynyl group, 2-cyclobutynyl group or the like [the alkenyl group may have substituents such as cyclic C3 to C6 alkyl group (e.g. cyclopropyl group, cyclobutyl group, cyclopentyl group or cyclohexyl group), tri(straight chain or branched chain C1 to C6 alkyl)silyl group (e.g. trimethylsilyl group or tert-butyldimethylsilyl group), straight chain or branched chain C1 to C6 alkoxy group (e.g. methoxy group, ethoxy group, n-propoxy group or isopropoxy group), tri (straight chain or branched chain C1 to C6 alkyl)silyloxy group (e.g. trimethylsilyloxy group or tert-butyldimethylsilyloxy group), straight chain or branched chain C1 to C6 hydroxyalkyl group (e.g. hydroxymethyl group or hydroxyethyl group), straight chain or branched chain (C1 to C6 alkoxy)-(C1 to C6 alkyl) group (e.g. methoxymethyl group, methoxyethyl group or ethoxyethyl group), straight chain or branched chain C1 to C6 haloalkyl group (e.g. fluoromethyl group, difluoromethyl group or trifluoromethyl group), nitro group, phenyl group, phenoxy group, hetero-aryl group (e.g. pyridyl group, thienyl group or furanyl group), and the like]; tri(straight chain or branched chain C1 to C6 alkyl)silyl group such as trimethylsilyl group, tert-butyldimethylsilyl group or the like; hydroxyl group; straight chain or branched chain C1 to C6 alkoxy group such as methoxy group, ethoxy group, n-propoxy group, isopropoxy group or the like; tri(straight chain or branched chain C1 to C6 alkyl)silyloxy group such as trimethylsilyloxy group, tert-butyldimethylsilyloxy group or the like; straight chain or branched chain C1 to C6 hydroxyalkyl group such as hydroxymethyl group, hydroxyethyl group or the like; straight chain or branched chain (C1 to C6 alkoxy)-(C1 to C6 alkyl) group such as methoxymethyl group, methoxyethyl group, ethoxyethyl group or the like; carboxyl group or metal salt thereof; (C1 to C6 alkoxy having the above meaning)carbonyl group; amino group; (C1 to C6 alkyl having the above meaning) amino group; (C1 to C6 alkyl having the above meaning) carbonylamino group; halogen atom; nitro group; phenyl group [the phenyl group may have substituents such as straight chain or branched chain C3 to C6 alkyl group (e.g. methyl group, ethyl group, n-propyl group, isopropyl group, n-butyl group, sec-butyl group, tert-butyl group, n-pentyl group or n-hexyl group), cyclic C1 to C6 alkyl group (e.g. cyclopropyl group, cyclobutyl group, cyclopentyl group or 3-cyclohexyl group), tri(straight chain or branched chain C1 to C6 alkyl)silyl group (e.g. trimethylsilyl group or tert-butyldimethylsilyl group), straight chain or branched chain C1 to C6 alkoxy group (e.g. methoxy group, ethoxy group, n-propoxy group or isopropoxy group), tri (straight chain or branched chain C1 to C6 alkyl)silyloxy group (e.g. trimethylsilyloxy group or tert-butyldimethylsilyloxy group), straight chain or branched chain C1 to C6 hydroxyalkyl group (e.g. hydroxymethyl group or hydroxyethyl group), straight chain or branched chain (C1 to C6 alkoxy)-(C1 to C6 alkyl) group (e.g. methoxymethyl group, methoxyethyl group or ethoxyethyl group), carboxyl group or metal salt thereof, halogen atom, nitro group, phenyl group, phenoxy group, hetero-aryl group (e.g. pyridyl group, thienyl group or furanyl group), and the like]; phenoxy group [the phenoxy group may have substituents such as straight chain or branched chain C1 to C6 alkyl group (e.g. methyl group, ethyl group, n-propyl group, isopropyl group, n-butyl group, sec-butyl group, tert-butyl group, n-pentyl group or n-hexyl group), cyclic C3 to C6 alkyl group (e.g. cyclopropyl group, cyclobutyl group, cyclopentyl group or cyclohexyl group), tri(straight chain or branched chain C1 to C6 alkyl) silyl group (e.g. trimethylsilyl group or tert-butyldimethylsilyl group), hydroxyl group, straight chain or branched chain C1 to C6 alkoxy group (e.g. methoxy group, ethoxy group, n-propoxy group or isopropoxy group), tri(straight chain or branched chain C1 to C6 alkyl)silyloxy group (e.g. trimethylsilyloxy group or tert-butyldimethylsilyloxy group), straight chain or branched chain C1 to C6 hydroxyalkyl group (e.g. hydroxymethyl group or hydroxyethyl group), straight chain or branched chain (C1 to C6 alkoxy)-(C1 to C6 alkyl) group (e.g. methoxymethyl group, methoxyethyl group or ethoxyethyl group), carboxyl group or metal salt thereof, halogen atom, nitro group, phenyl group, phenoxy group, hetero-aryl group (e.g. pyridyl group, thienyl group or furanyl group), and the like]; or hetero-aryl group (e.g. pyridyl group, thienyl group or furanyl group) [the hetero-aryl group may have substituents such as straight chain or branched chain C1 to C6 alkyl group (e.g. methyl group, ethyl group, n-propyl group, isopropyl group, n-butyl group, sec-butyl group, tert-butyl group, n-pentyl group or n-hexyl group), cyclic C3 to C6 alkyl group (e.g. cyclopropyl group, cyclobutyl group, cyclopentyl group or cyclohexyl group), tri(straight chain or branched chain C1 to C6 alkyl)silyl group (e.g. trimethylsilyl group or tert-butyldimethylsilyl group), hydroxyl group, straight chain or branched chain C1 to C6 alkoxy group (e.g. methoxy group, ethoxy group, n-propoxy group or isopropoxy group), tri(straight chain or branched chain C1 to C6 alkyl)silyloxy group (e.g. trimethylsilyloxy group or tert-butyldimethylsilyloxy group), straight chain or branched chain C1 to C6 hydroxyalkyl group (e.g. hydroxymethyl group or hydroxyethyl group), straight chain or branched chain (C1 to C6 alkoxy)-(C1 to C6 alkyl) group (e.g. methoxymethyl group, methoxyethyl group or ethoxyethyl group), carboxyl group or metal salt thereof, halogen atom, nitro group, phenyl group, phenoxy group, hetero-aryl group (e.g. pyridyl group, thienyl group or furanyl group), and the like]. Two of $R_5$, $R_6$, $R_7$, $R_8$ and $R_9$ may be bonded with each other to form a ring.

As specific examples of the benzylidenecyclohexanone compound represented by the general formula (1), usable in the reaction, there can be mentioned 2-benzylidenecyclohexanone, 2-(2-methylbenzylidene)cyclohexanone, 2-(2-ethylbenzylidene)cyclohexanone, 2-(2-n-propylbenzylidene)cyclohexanone, 2-(2-isopropylbenzylidene)cyclohexanone, 2-(2-n-butylbenzylidene)cyclohexanone, 2-(2-n-hexylbenzylidene)cyclohexanone, 2-(2-cyclohexylbenzylidene)cyclohexanone, 2-(2-phenylbenzylidene)cyclohexanone, 2-(2-benzylbenzylidene)cyclohexanone, 2-(2-pyridylbenzylidene)cyclohexanone, 2-(2-thienylbenzylidene)cyclohexanone, 2-(2-furylbenzylidene) cyclohexanone, 2-(2-methoxybenzylidene)cyclohexanone, 2-(2-ethoxybenzylidene)cyclohexanone, 2-(2-n-propoxybenzylidene)cyclohexanone, 2-(2-isopropoxybenzylidene) cyclohexanone, 2-(2-n-butoxybenzylidene)cyclohexanone, 2-(2-n-hexyloxybenzylidene)cyclohexanone, 2-(2-cyclohexyloxybenzylidene)cyclohexanone, 2-(2-phenoxybenzylidene)cyclohexanone, 2-(2-benzyloxybenzylidene)cyclohexanone, 2-(3-methylbenzylidene)cyclohexanone, 2-(3-ethylbenzylidene)cyclohexanone, 2-(3-n-propylbenzylidene)cyclohexanone, 2-(3-isopropylbenzylidene)cyclohexanone, 2-(3-n-butylbenzylidene)-cyclohexanone, 2-(3-n-hexylbenzylidene)cyclohexanone, 2-(3-cyclohexylbenzylidene)cyclohexanone, 2-(3-phenylbenzylidene)cyclohexanone, 2-(3-benzylbenzylidene)cyclohexanone, 2-(3-methoxybenzylidene)cyclohexanone, 2-(3-ethoxybenzylidene)cyclohexanone, 2-(3-n-propoxybenzylidene)cyclohexanone, 2-(3-isopropoxybenzylidene)cyclohexanone, 2-(3-n-butoxybenzylidene)cyclohexanone, 2-(3-n-hexyloxybenzylidene)cyclohexanone, 2-(3-cyclohexyloxybenzylidene)cyclohexanone, 2-(3-phenoxybenzylidene)cyclohexanone, 2-(3-benzyloxybenzylidene)cyclohexanone, 2-(4-methylbenzylidene)cyclohexanone, 2-(4-ethylbenzylidene) cyclohexanone, 2-(4-n-propylbenzylidene)cyclohexanone, 2-(4-isopropylbenzylidene)cyclohexanone, 2-(4-n-butylbenzylidene)cyclohexanone, 2-(4-n-hexylbenzylidene)cyclohexanone, 2-(4-cyclohexylbenzylidene)cyclohexanone, 2-(4-phenylbenzylidene)cyclohexanone, 2-(4-benzylbenzylidene)cyclohexanone, 2-(4-methoxybenzylidene)cyclohexanone, 2-(4-ethoxybenzylidene)cyclohexanone, 2-(4-n-propoxybenzylidene)cyclohexanone, 2-(4-isopropoxybenzylidene)cyclohexanone, 2-(4-n-butoxybenzylidene)cyclohexanone, 2-(4-n-hexyloxybenzylidene)cyclohexanone, 2-(4-cyclohexyloxybenzylidene)cyclohexanone, 2-(4-phenoxybenzylidene)cyclohexanone, 2-(4- benzyloxybenzylidene)cyclohexanone, 2-(4-methylthiobenzylidene)cyclohexanone, 2-(4-ethylthiobenzylidene)cyclohexanone, 2-(4-n-propylthiobenzylidene)cyclohexanone, 2-(4-isopropylthiobenzylidene)cyclohexanone, 2-(4-n-butylthiobenzylidene)cyclohexanone, 2-(4-isobutylthiobenzylidene)cyclohexanone, 2-(2,3-dimethylbenzylidene)cyclohexanone, 2-(2,4-dimethylbenzylidene)cyclohexanone, 2-(2,6-dimethylbenzylidene)cyclohexanone, 2-(3,4-dimethylbenzylidene)cyclohexanone, 2-(2,3-dimethoxybenzylidene)cyclohexanone, 2-(2,4-dimethoxybenzylidene)cyclohexanone, 2-(2,6-dimethoxybenzylidene)cyclohexanone, 2-(3,4-dimethoxybenzylidene)cyclohexanone, 2-benzylidene-3-methylcyclohexanone, 2-benzylidene-4-methylcyclohexanone, 2-benzylidene-5-methylcyclohexanone, 2-benzylidene-6-methylcyclohexanone, 2-benzylidene-3-ethyl-cyclohexanone, 2-benzylidene-4-ethylcyclohexanone, 2-benzylidene-5-ethylcyclohexanone, 2-benzylidene-3-cyclo-pentylcyclohexanone, 2-benzylidene-4-cyclopentylcyclohexanone, 2-benzylidene-5-cyclopentylcyclohexanone, 2-benzylidene-3-cyclohexylcyclohexanone, 2-benzylidene-4-cyclohexylcyclohexanone, 2-benzylidene-5-cyclohexylcyclohexanone, 2-benzylidene-3-trimethylsilylcyclohexanone, 2-benzylidene-4-trimethylsilylcyclohexanone, 2-benzylidene-5-trimethylsilylcyclohexanone, 2-benzylidene-3-methoxycyclohexanone, 2-benzylidene-4-methoxycyclohexanone, 2-benzylidene-5-methoxycyclohexanone, 2-benzylidene-3-trimethylsilyloxycyclohexanone, 2-benzylidene-4-trimethylsilyloxycyclohexanone, 2-benzylidene-5-trimethylsilyloxycyclohexanone, 2-benzylidene-3-hydroxymethylcyclohexanone, 2-benzylidene-4-hydroxymethylcyclohexanone, 2-benzylidene-5-hydroxymethylcyclohexanone, 2-benzylidene-3-methoxymethylcyclohexanone, 2-benzylidene-4-methoxymethylcyclohexanone, 2-benzylidene-5-methoxymethylcyclohexanone, 2-benzylidene-3-phenylcyclohexanone, 2-benzylidene-4-phenylcyclohexanone, 2-benzylidene-5-phenylcyclohexanone, 2-benzylidene-3-phenoxycyclohexanone, 2-benzylidene-4-phenoxycyclohexanone, 2-benzylidene-5-phenoxycyclohexanone, 2-benzylidene-3-pyridylcyclohexanone, 2-benzylidene-4-pyridylcyclohexanone, 2-benzylidene-5-pyridylcyclohexanone, 2-benzylidene-3-thienylcyclohexanone, 2-benzylidene-4-thienylcyclohexanone, 2-benzylidene-5-thienylcyclohexanone, 2-benzylidene-3-furanylcyclohexanone, 2-benzylidene-4-furanylcyclohexanone, 2-benzylidene-5-furanylcyclohexanone, 2-(2-methoxybenzylidene)-3-methylcyclohexanone, 2-(2-methoxybenzylidene)-4-methylcyclohexanone, 2-(2-methoxybenzylidene)-5-methylcyclohexanone, 2-(2-methoxybenzylidene)-3-ethylcyclohexanone, 2-(2-methoxybenzylidene)-4-ethylcyclohexanone, 2-(2-methoxybenzylidene)-5-ethylcyclohexanone, 2-(2-methoxybenzylidene)-3-cyclopentylcyclohexanone, 2-(2-methoxybenzylidene)-4-cyclopentylcyclohexanone, 2-(2-methoxybenzylidene)-5-cyclopentylcyclohexanone, 2-(2-methoxybenzylidene)-3-cyclohexylcyclohexanone, 2-(2-methoxybenzylidene)-4-cyclohexylcyclohexanone, 2-(2-methoxybenzylidene)-5-cyclohexylcyclohexanone, 2-(2-methoxybenzylidene)-3-trimethylsilylcyclohexanone, 2-(2-methoxybenzylidene)-4-trimethylsilylcyclohexanone, 2-(2-methoxybenzylidene)-5-trimethylsilylcyclohexanone, 2-(2-methoxybenzylidene)-3-methoxycyclohexanone, 2-(2-methoxybenzylidene)-4-methoxycyclohexanone, 2-(2-methoxybenzylidene)-5-methoxycyclohexanone, 2-(2-methoxybenzylidene)-3-trimethylsilyloxycyclohexanone, 2-(2-methoxybenzylidene)-4-trimethylsilyloxycyclohexanone, 2-(2-methoxybenzylidene)-5-trimethylsilyloxycyclohexanone, 2-(2-methoxybenzylidene)-3-hydroxymethylcyclohexanone, 2-(2-methoxybenzylidene)-4-hydroxymethylcyclohexanone, 2-(2-methoxybenzylidene)-5-hydroxymethylcyclohexanone, 2-(2-methoxybenzylidene)-3-methoxymethylcyclohexanone, 2-(2-methoxybenzylidene)-4-methoxymethylcyclohexanone, 2-(2-methoxybenzylidene)-5-methoxymethylcyclohexanone, 2-(2-methoxybenzylidene)-3-phenylcyclohexanone, 2-(2-methoxybenzylidene)-4-phenylcyclohexanone, 2-(2-methoxybenzylidene)-5-phenylcyclohexanone, 2-(2-methoxybenzylidene)-3-phenoxycyclohexanone, 2-(2-methoxybenzylidene)-4-phenoxycyclohexanone, 2-(2-methoxybenzylidene)-5-phenoxycyclohexanone, 2-(2-methoxybenzylidene)-3-pyridylcyclohexanone, 2-(2-methoxybenzylidene)-4-pyridylcyclohexanone, 2-(2-methoxybenzylidene)-5-pyridylcyclohexanone, 2-(2-methoxybenzylidene)-3-thienylcyclohexanone, 2-(2-methoxybenzylidene)-4-thienylcyclohexanone, 2-(2-methoxybenzylidene)-5-thienylcyclohexanone, 2-(2-methoxybenzylidene)-3-furanylcyclohexanone, 2-(2-methoxybenzylidene)-4-furanylcyclohexanone, 2-(2-methoxybenzylidene)-5-furanylcyclohexanone, 2-(3-methoxybenzylidene)-3-methylcyclohexanone, 2-(3-methoxybenzylidene)-4-methylcyclohexanone, 2-(3-methoxybenzylidene)-5-methylcyclohexanone, 2-(3-methoxybenzylidene)-3-ethylcyclohexanone, 2-(3-methoxybenzylidene)-4-ethylcyclohexanone, 2-(3-methoxybenzylidene)-5-ethylcyclohexanone, 2-(3-methoxybenzylidene)-3-cyclopentylcyclohexanone, 2-(3-methoxybenzylidene)-4-cyclopentylcyclohexanone, 2-(3-methoxybenzylidene)-5-cyclopentylcyclohexanone, 2-(3-methoxybenzylidene)-3-cyclohexylcyclohexanone, 2-(3-methoxybenzylidene)-4-cyclohexylcyclohexanone, 2-(3-methoxybenzylidene)-5-cyclohexylcyclohexanone, 2-(3-methoxybenzylidene)-3-trimethylsilylcyclohexanone, 2-(3-methoxybenzylidene)-4-trimethylsilylcyclohexanone, 2-(3-methoxybenzylidene)-5-trimethylsilylcyclohexanone, 2-(3-methoxybenzylidene)-3-methoxycyclohexanone, 2-(3-methoxybenzylidene)-4-methoxycyclohexanone, 2-(3-methoxybenzylidene)-5-methoxycyclohexanone, 2-(3-methoxybenzylidene)-3-trimethylsilyloxycyclohexanone, 2-(3-methoxybenzylidene)-4-trimethylsilyloxycyclohexanone, 2-(3-methoxybenzylidene)-5-trimethylsilyloxycyclohexanone, 2-(3-methoxybenzylidene)-3-hydroxymethylcyclohexanone, 2-(3-methoxybenzylidene)-4-hydroxymethylcyclohexanone, 2-(3-methoxybenzylidene)-5-hydroxymethylcyclohexanone, 2-(3-methoxybenzylidene)-3-methoxymethylcyclohexanone, 2-(3-methoxybenzylidene)-4-methoxymethylcyclohexanone, 2-(3-methoxybenzylidene)-5-methoxymethylcyclohexanone, 2-(3-methoxybenzylidene)-3-phenylcyclohexanone, 2-(3-methoxybenzylidene)-4-phenylcyclohexanone, 2-(3-methoxybenzylidene)-5-phenylcyclohexanone, 2-(3-methoxybenzylidene)-3-phenoxycyclohexanone, 2-(3-methoxybenzylidene)-4-phenoxycyclohexanone, 2-(3-methoxybenzylidene)-5-phenoxycyclohexanone, 2-(3-methoxybenzylidene)-3-pyridylcyclohexanone, 2-(3-methoxybenzylidene)-4-pyridylcyclohexanone, 2-(3-methoxybenzylidene)-5-pyridylcyclohexanone, 2-(3-methoxybenzylidene)-3-thienylcyclohexanone, 2-(3-methoxybenzylidene)-4-thienylcyclohexanone, 2-(3-methoxybenzylidene)-5-thienylcyclohexanone, 2-(3-methoxybenzylidene)-3-furanylcyclohexanone, 2-(3- methoxybenzylidene)-4-furanylcyclohexanone, 2-(3-methoxybenzylidene)-5-furanylcyclohexanone, 2-(4-methoxybenzylidene)-3-methylcyclohexanone, 2-(4-methoxybenzylidene)-4-methylcyclohexanone, 2-(4-methoxybenzylidene)-5-methylcyclohexanone, 2-(4-methoxybenzylidene)-3-ethylcyclohexanone, 2-(4-methoxybenzylidene)-4-ethylcyclohexanone, 2-(4-methoxybenzylidene)-5-ethylcyclohexanone, 2-(4-methoxybenzylidene)-3-cyclopentylcyclohexanone, 2-(4-methoxybenzylidene)-4-cyclopentylcyclohexanone, 2-(4-methoxybenzylidene)-5-cyclopentylcyclohexanone, 2-(4-methoxybenzylidene)-3-cyclohexylcyclohexanone, 2-(4-methoxybenzylidene)-4-cyclohexylcyclohexanone, 2-(4-methoxybenzylidene)-5-cyclohexylcyclohexanone, 2-(4-methoxybenzylidene)-3-trimethylsilylcyclohexanone, 2-(4-methoxybenzylidene)-4-trimethylsilylcyclohexanone, 2-(4-methoxybenzylidene)-5-trimethylsilylcyclohexanone, 2-(4-methoxybenzylidene)-3-methoxycyclohexanone, 2-(4-methoxybenzylidene)-4-methoxycyclohexanone, 2-(4-methoxybenzylidene)-5-methoxycyclohexanone, 2-(4-methoxybenzylidene)-3-trimethylsilyloxycyclohexanone, 2-(4-methoxybenzylidene)-4-trimethylsilyloxycyclohexanone, 2-(4-methoxybenzylidene)-5-trimethylsilyloxycyclohexanone, 2-(4-methoxybenzylidene)-3-hydroxymethylcyclohexanone, 2-(4-methoxybenzylidene)-4-hydroxymethylcyclohexanone, 2-(4-methoxybenzylidene)-5-hydroxymethylcyclohexanone, 2-(4-methoxybenzylidene)-3-methoxymethylcyclohexanone, 2-(4-methoxybenzylidene)-4-methoxymethylcyclohexanone, 2-(4-methoxybenzylidene)-5-methoxymethylcyclohexanone, 2-(4-methoxybenzylidene)-3-phenylcyclohexanone, 2-(4-methoxybenzylidene)-4-phenylcyclohexanone, 2-(4-methoxybenzylidene)-5-phenylcyclohexanone, 2-(4-methoxybenzylidene)-3-phenoxycyclohexanone, 2-(4-methoxybenzylidene)-4-phenoxycyclohexanone, 2-(4-methoxybenzylidene)-5-phenoxycyclohexanone, 2-(4-methoxybenzylidene)-3-pyridylcyclohexanone, 2-(4-methoxybenzylidene)-4-pyridylcyclohexanone, 2-(4-methoxybenzylidene)-5-pyridylcyclohexanone, 2-(4-methoxybenzylidene)-3-thienylcyclohexanone, 2-(4-methoxybenzylidene)-4-thienylcyclohexanone, 2-(4-methoxybenzylidene)-5-thienylcyclohexanone, 2-(4-methoxybenzylidene)-3-furanylcyclohexanone, 2-(4-methoxybenzylidene)-4-furanylcyclohexanone, 2-(4-methoxybenzylidene)-5-furanylcyclohexanone, 2-(2-fluorobenzylidene)cyclohexanone, 2-(3-fluorobenzylidene)cyclohexanone, 2-(4-fluorobenzylidene)cyclohexanone, 2-(2-chlorobenzylidene)cyclohexanone, 2-(3-chlorobenzylidene)cyclohexanone, 2-(4-chlorobenzylidene)cyclohexanone, 2-(2-bromobenzylidene)cyclohexanone, 2-(3-bromobenzylidene)cyclohexanone, 2-(4-bromobenzylidene)cyclohexanone, 2-(2-iodobenzylidene)cyclohexanone, 2-(3-iodobenzylidene)cyclohexanone, 2-(4-iodobenzylidene)cyclohexanone, 2-(2-nitrobenzylidene)cyclohexanone, 2-(3-nitrobenzylidene)cyclohexanone, 2-(4-nitrobenzylidene)cyclohexanone, 2-(2-vinylbenzylidene)cyclohexanone, 2-(3-vinylbenzylidene)cyclohexanone, 2-(4-vinylbenzylidene)cyclohexanone, 2-(2-ethynylbenzylidene)cyclohexanone, 2-(3-ethynylbenzylidene)cyclohexanone, and 2-(4-ethynylbenzylidene)cyclohexanone. As preferred examples, there can be mentioned 2-benzyldenecyclohexanone, 2-(4-methylbenzylidene)cyclohexanone, 2-(4-methoxybenzylidene)cyclohexanone, 2-(4-chlorobenzylidene)cyclohexanone, 2-(4-fluorobenzylidene)cyclohexanone, 2-(4-methylbenzylidene)-4-methylcyclohexanone, 2-(4-methoxybenzylidene)-4-methylcylcohexanone, 2-(4-chlorobenzylidene)-4-methylcyclohexanone, 2-(4-fluorobenzylidene)-4-methylcyclohexanone, 2-(4-methylbenzylidene)-4-chlorocyclohexanone, 2-(4-methoxybenzylidene)-4-chlorocyclohexanone, 2-(4-chlorobenzylidene)-4-chlorocyclohexanone, 2-(4-fluorobenzylidene)-4-chlorocyclohexanone, 2-(4-methylbenzylidene)-4-fluorocyclohexanone, 2-(4-methoxybenzylidene)-4-fluorocyclohexanone, 2-(4-chlorobenzylidene)-4-fluorocyclohexanone, and 2-(4-fluorobenzylidene)-4-fluoromethylcyclohexanone. Of these, particularly preferred are 2-benzylidenecyclohexanone, 2-(4-methylbenzylidene)cyclohexanone, 2-(4-methoxybenzylidene)cyclohexanone, 2-(4-chlorobenzylidene)cyclohexanone, and 2-(4-fluorobenzylidene)cyclohexanone.

These benzylidenecyclohexanone compounds represented by the general formula (1) include some novel compounds; however, they can be easily produced from a cyclohexanone compound represented by the general formula (3) and a benzaldehyde compound represented by the general formula (4), according to the process described later.

Successively, description is made on the reaction of the benzylidenecyclohexanone compound represented by the general formula (1), conducted in the presence of a dehydrogenating agent.

The reaction can be conducted in the presence of a dehydrogenating agent. The dehydrogenating agent can be any substance as long as it can conduct dehydrogenation from the benzylidenecyclohexanone compound represented by the general formula (1), and there can be mentioned, for example, a palladium catalyst or sulfur.

Description is made first on the reaction using a palladium catalyst as a dehydrogenating agent.

The palladium catalyst used in the reaction as a dehydrogenating agent can be any of a heterogeneous palladium catalyst and a homogeneous palladium catalyst as long as it can conduct dehydrogenation from the benzylidenecyclohexanone compound represented by the general formula (1). The heterogeneous palladium catalyst may have any shape and can be a powder, a crushed form, pellets, a spherical form, etc.

Therefore, as specific examples of the palladium catalyst used in the reaction, there can be mentioned heterogeneous palladium catalysts such as palladium carbon, palladium-loaded alumina, palladium-loaded barium sulfate, palladium-loaded calcium carbonate, palladium-loaded zeolite, palladium-loaded silica, palladium-loaded silica-alumina, palladium oxide, palladium black and the like; and homogeneous palladium catalysts such as palladium (II) chloride, palladium (II) nitrate, palladium (II) acetate, palladium (II) trifluoroacetate, tetraanminepalladium chloride (II), tetraanminepalladium nitrate (II), dinitrodianminepalladium (II), dichlorobis(triphenylphosphine)palladium (II), tetrakis(triphenylphosphine)palladium (0), di-μ-chlorobis[(η-allyl)palladium (II)], bis(acetylacetonato)palladium (II), dichlorobis(benzonitrile)palladium (II), palladium (II) propionate, tris(dibenzylideneacetone)dipalladium (0), [1,1'-bis(diphenylphosphino)ferrocene]palladium (II) chloride and the like. These palladium catalysts may be used alone or in admixture of any mixing proportions.

These palladium catalysts are known compounds.

Use of heterogeneous palladium catalyst such as palladium carbon, palladium-loaded alumina or the like is preferred in view of the easy recovery of expensive palladium catalyst after the reaction using the catalyst. Use of palladium carbon is preferred particularly, because it is marketed in various palladium contents (loaded ratios) and easily obtainable, is easy to handle, and is high in reactivity.

With respect to the molar ratio of the palladium catalyst used in the reaction, the reaction proceeds at any molar ratio of palladium catalyst relative to the benzylidenecyclohexanone compound represented by the general formula (1). However, The molar ratio is, for example, ordinarily 0.0001 to 1.0 mole, preferably 0.001 to 0.1 mole, more preferably 0.001 to 0.05 mole relative to 1 mole of the benzylidenecyclohexanone compound represented by the general formula (1).

The reaction using the palladium catalyst is preferably conducted using a solvent, for smooth progress of the reaction. The solvent used in the reaction may be any solvent as long as it does not hinder the reaction. There can be mentioned, for example, ethers such as diphenyl ether, anisole and the like; aromatic hydrocarbons such as mesitylene, xylene and the like; alcohols such as 2-ethyl-1-hexanol, ethylene glycol and the like; aprotic polar solvents such as tetramethylurea, hexamethylphosphoric triamide (HMPA), propylene carbonate and the like; aliphatic hydrocarbons such as pentane, n-hexane and the like; olefins such as diethyl maleate, 1,5,9-cyclododecatriene, ethyl cinnamate and the like; aromatic nitro compounds such as nitrobenzene, 4-nitrotoluene and the like; aromatic halogen compounds such as chlorobenzene, o-dichlorobenzene and the like; and aromatic carbonyl compounds such as benzaldehyde, acetophenone and the like. Use of ether such as diphenyl ether, anisole or the like is preferred, and use of diphenyl ether is referred particularly. The solvents can be used singly or in admixture of any mixing proportions. The amount of the solvent used may be any level as long as it allows for sufficient stirring of the reaction system; however, it is ordinarily 0.05 to 10 liters, preferably 0.5 to 2 liters relative to 1 mole of the benzylidenecyclohexanone compound represented by the general formula (1).

The temperature of the reaction using the palladium catalyst is, for example, 0° C. to the refluxing temperature of the solvent used, preferably 150 to 280° C., more preferably 150 to 230° C.

When it is intended to conduct the reaction using the palladium catalyst, particularly at 230° C. or lower (e.g. 150 to 230° C.), preferably at 200° C. or lower (e.g. 150 to 200° C., the aim can be achieved by, to suppress the side reaction caused by the hydrogen formed as a by-product in the reaction, allowing a hydrogen acceptor to be present in the reaction system [the hydrogen acceptor is a substance which can be per se reduced by hydrogen and can easily be hydrogenated in preference to the reaction intermediate formed in the course of the reaction from the benzylidenecyclohexanone compound represented by the general formula (1) to the 2-benzylphenol compound represented by the general formula (2)].

The hydrogen acceptor used in the above case may be any substance which can hinder the following reverse reaction of the intended reaction from the benzylidenecyclohexanone compound of the general formula (1) to the 2-benzylphenol compound of the general formula (2). That is, as the intended reaction from the benzylidenecyclohexanone compound of the general formula (1) to the 2-benzylphenol compound of the general formula (2) proceeds (a dehydrogenation reaction proceeds), hydrogen is generated in the reaction system; this hydrogen hydrogenates the reaction intermediate formed by the dehydrogenation reaction and there takes place a reverse reaction of the dehydrogenation reaction; in this case, if a hydrogen acceptor is present in the reaction system, the hydrogen acceptor is hydrogenated in preference to the reaction intermediate and the reverse reaction is hindered. As specific examples of the hydrogen acceptor, there can be mentioned olefins such as diethyl maleate, 1,5,9-cyclododecatriene, ethyl cinnamate and the like; aromatic nitro compounds such as nitrobenzene, 4-nitrotoluene and the like; aromatic halogen compounds such as chlorobenzene, o-dichlorobenzene and the like; aromatic carbonyl compounds such as benzaldehyde, acetophenone and the like; and so forth, all exemplified above as a solvent. The amount of the hydrogen acceptor used is ordinarily 0.5 mole to the excessive amount allowed as solvent, preferably 1 mole to the excessive amount allowed as solvent, relative to 1 mole of the benzylidenecyclohexanone compound represented by the general formula (1). Use of olefin such as diethyl maleate, 1,5,9-cyclododecatriene, ethyl cinnamate or the like is preferred, and use of diethyl maleate as a solvent gives a more preferred result.

The time of the reaction using the palladium catalyst is not particularly restricted. However, the time is preferred to be 1 to 30 hours from the standpoint of, for example, suppression of by-product formation.

Next, description is made on the reaction of the benzylidenecyclohexanone compound represented by the general formula (1) using sulfur as a dehydrogenating agent.

Use of sulfur is particularly preferred in the reaction of the benzylidenecyclohexanone compound represented by the general formula (1) when the benzylidenecyclohexanone compound represented by the general formula (1) has a functional group (typified by halogen atom, nitro group or the like) which may be influenced by the palladium catalyst.

The reaction using sulfur proceeds at any molar ratio of sulfur relative to the benzylidenecyclohexanone compound represented by the general formula (1). However, the molar ratio is, for example, ordinarily 0.1 to 5.0 moles, preferably 1.0 to 3.0 moles, more preferably 1.1 to 2.0 moles relative to 1 mole of the benzylidenecyclohexanone compound represented by the general formula (1).

The reaction using sulfur is preferably conducted using a solvent, for smooth progress of the reaction. The solvent used in the reaction may be any solvent as long as it does not hinder the reaction. There can be mentioned, for example, aromatic halogen compounds such as 3,4-dichlorotoluene, o-dichlorobenzene and the like; ethers such as diphenyl ether, anisole and the like; aromatic hydrocarbons such as mesitylene, xylene and the like; alcohols such as ethanol, 2-ethyl-1-hexanol, ethylene glycol and the like; aprotic polar solvents such as tetramethylurea, hexamethylphosphoric triamide (HMPA), propylene carbonate and the like; and aliphatic hydrocarbons such as pentane, n-hexane and the like. Use of aromatic halogen compound such as 3,4-dichlorotoluene, o-dichlorobenzene or the like is preferred, and use of 3,4-dichlorotoluene is referred particularly. The solvents can be used singly or in admixture of any mixing proportions. The amount of the solvent used may be any level as long as it allows for sufficient stirring of the reaction system; however, it is ordinarily 0.05 to 10 liters, preferably 0.3 to 2 liters relative to 1 mole of the benzylidenecyclohexanone compound represented by the general formula (1).

The temperature of the reaction using sulfur is, for example, 150° C. to the refluxing temperature of the solvent used, preferably 180 to 250° C.

The time of the reaction using sulfur is not particularly restricted. However, the time is preferred to be 1 to 30 hours from the standpoint of, for example, suppression of by-product formation.

As described above, according to the present process, there can be produced a 2-benzylphenol compound represented by the general formula (2) at a high selectivity and easily, under mild conditions without using any special reactor. The 2-benzylphenol compound of the general formula (2) produced by the present process include some novel compounds. As necessary, the catalyst may be used in a fixed bed or some device may be considered for the reactor. The obtained 2-benzylphenol compound of the general formula (2) is useful as an intermediate for medicine, agricultural chemical, etc.

The benzylidenecyclohexanone compound represented by the general formula (1), used in the present process can be obtained easily, for example, by subjecting, to a condensation reaction in the presence of a base, a cyclohexanone compound represented by the general formula (3) and a benzaldehyde compound represented by the general formula (4).

Description is made of the cyclohexanone compound represented by the general formula (3).

The $R_1$, $R_2$, $R_3$ and $R_4$ in the general formula (3) have the same definitions as given above. As specific examples of the cyclohexanone of the general formula (3) usable in the condensation reaction, there can be mentioned cyclohexanone, 2-methylcyclohexanone, 3-methylcyclohexanone, 4-methylcyclohexanone, 2-ethylcyclohexanone, 3-ethylcyclohexanone, 4-ethylcyclohexanone, 2-cyclopentylcyclohexanone, 3-cyclopentylcyclohexanone, 4-cyclopentylcyclohexanone, 2-cyclohexylcyclohexanone, 3-cyclohexylcyclohexanone, 4-cyclohexylcyclohexanone, 2-trimethylsilylcyclohexanone, 3-trimethylsilylcyclohexanone, 4-trimethylsilylcyclohexanone, 2-methoxycyclohexanone, 3-methoxycyclohexanone, 4-methoxycyclohexanone, 2-trimethylsilyloxycyclohexanone, 3-trimethylsilyloxycyclohexanone, 4-trimethylsilyloxycyclohexanone, 2-hydroxymethylcyclohexanone, 3-hydroxymethylcyclohexanone, 4-hydroxymethylcyclohexanone, 2-methoxymethylcyclohexanone, 3-methoxymethylcyclohexanone, 4-methoxymethylcyclohexanone, 2-phenylcyclohexanone, 3-phenylcyclohexanone, 4-phenylcyclohexanone, 2-phenoxycyclohexanone, 3-phenoxycyclohexanone, 4-phenoxycyclohexanone, 2-pyridylcyclohexanone, 3-pyridylcyclohexanone, 4-pyridylcyclohexanone, 2-thienylcyclohexanone, 3-thienylcyclohexanone, 4-thienylcyclohexanone, 2-furanylcyclohexanone, 3-furanylcyclohexanone and 4-furanylcyclohexanone. These compounds may have substituents such as straight chain or branched chain C1 to C6 alkyl group (e.g. methyl group, ethyl group, n-propyl group, isopropyl group, n-butyl group, sec-butyl group, tert-butyl group, n-pentyl group or n-hexyl group), cyclic C3 to C6 alkyl group (e.g. cyclopropyl group, cyclobutyl group, cyclopentyl group or cyclohexyl group), tri(straight chain or branched chain C1 to C6 alkyl)silyl group (e.g. trimethylsilyl group or tert-butyldimethylsilyl group), straight chain or branched C1 to C6 alkoxy group (e.g. methoxy group, ethoxy group, n-propoxy group or isopropoxy group), tri(straight chain or branched chain C1 to C6 alkyl)silyloxy group (e.g. trimethylsilyloxy group or tert-butyldimethylsilyloxy group), straight chain or branched chain C1 to C6 hydroxyalkyl group (e.g. hydroxymethyl group or hydroxyethyl group), straight chain or branched chain (C1 to C6 alkoxy)-(C1 to C6 alkyl) group (e.g. methoxymethyl group, methoxyethyl group or ethoxyethyl group), phenyl group, phenoxy group, hetero-aryl group (e.g. pyridyl group, thienyl group or furanyl group), and the like. As preferred examples of the cyclohexanone compound represented by the general formula (3), there can be mentioned cyclohexanone and 4-methylcyclohexanone.

Then, description is made on the benzaldehyde compound represented by the general formula (4).

The $R_5$, $R_6$, $R_7$, $R_8$ and $R_9$ of the general formula (4) have the same definitions as given above. As specific examples of the benzaldehyde of the general formula (4) usable in the condensation reaction, there can be mentioned benzaldehyde, 2-methylbenzaldehyde, 3-methylbenzaldehyde, 4-methylbenzaldehyde, 2-ethylbenzaldehyde, 3-ethylbenzaldehyde, 4-ethylbenzaldehyde, 2-cyclopentylbenzaldehyde, 3-cyclopentylbenzaldehyde, 4-cyclopentylbenzaldehyde, 2-cyclohexylbenzaldehyde, 3-cyclohexylbenzaldehyde, 4-cyclohexylbenzaldehyde, 2-trimethylsilylbenzaldehyde, 3-trimethylsilylbenzaldehyde, 4-trimethylsilylbenzaldehyde, 2-hydroxybenzaldehyde, 3-hydroxybenzaldehyde, 4-hydroxybenzaldehyde, 2-methoxybenzaldehyde, 3-methoxybenzaldehyde, 4-methoxybenzaldehyde, 2-trimethylsilyloxybenzaldehyde, 3-trimethylsilyloxybenzaldehyde, 4-trimethylsilyloxybenzaldehyde, 2-hydroxymethylbenzaldehyde, 3-hydroxymethylbenzaldehyde, 4-hydroxymethylbenzaldehyde, 2-methoxymethylbenzaldehyde, 3-methoxymethylbenzaldehyde, 4-methoxymethylbenzaldehyde, 2-phenylbenzaldehyde, 3-phenylbenzaldehyde, 4-phenylbenzaldehyde, 2-phenoxybenzaldehyde, 3-phenoxybenzaldehyde, 4-phenoxybenzaldehyde, 2-pyridylbenzaldehyde, 3-pyridylbenzaldehyde, 4-pyridylbenzaldehyde, 2-thienylbenzaldehyde, 3-thienylbenzaldehyde, 4-thienylbenzaldehyde, 2-furanylbenzaldehyde, 3-furanylbenzaldehyde, 4-furanylbenzaldehyde, 2-fluorobenzaldehyde, 3-fluorobenzaldehyde, 4-fluorobenzaldehyde, 2-chlorobenzaldehyde, 3-chlorobenzaldehyde, 4-chlorobenzaldehyde, 2-bromobenzaldehyde, 3-bromobenzaldehyde, 4-bromobenzaldehyde, 2-iodobenzaldehyde, 3-iodobenzaldehyde, 4-iodobenzaldehyde, 2-nitrobenzaldehyde, 3-nitrobenzaldehyde, 4-nitrobenzaldehyde, 2-vinylbenzaldehyde, 3-vinylbenzaldehyde, 4-vinylbenzaldehyde, 2-ethynylbenzaldehyde, 3-ethynylbenzaldehyde and 4-ethynylbenzaldehyde. These compounds may have substituents such as straight chain or branched chain C1 to C6 alkyl group (e.g. methyl group, ethyl group, n-propyl group, isopropyl group, n-butyl group, sec-butyl group, tert-butyl group, n-pentyl group or n-hexyl group), cyclic C3 to C6 alkyl group (e.g. cyclopropyl group, cyclopentyl group or cyclohexyl group), tri(straight chain or branched chain C1 to C6 alkyl) silyl group (e.g. trimethylsilyl group or tert-butyldimethylsilyl group), straight chain or branched C1 to C6 alkoxy group (e.g. methoxy group, ethoxy group, n-propoxy group or isopropoxy group), tri(straight chain or branched chain C1 to C6 alkyl)silyloxy group (e.g. trimethylsilyloxy group or tert-butyldimethylsilyloxy group), straight chain or branched chain C1 to C6 hydroxyalkyl group (e.g. hydroxymethyl group or hydroxyethyl group), straight chain or branched chain (C1 to C6 alkoxy)-(C1 to C6 alkyl) group (e.g. methoxymethyl group, methoxyethyl group or ethoxyethyl group), phenyl group, phenoxy group, hetero-aryl group (e.g. pyridyl group, thienyl group or furanyl group), and the like. As preferred examples of the benzaldehyde compound represented by the general formula (4), there can be mentioned benzaldehyde, 4-methylbenzaldehyde, 4-methoxybenzaldehyde, 4-chlorobenzaldehyde and 4-fluorobenzaldehyde.

The cyclohexanone compound represented by the general formula (3) and the benzaldehyde compound represented by the general formula (4) are each a known compound or can each be produced by a known process or a process conforming thereto.

The condensation reaction proceeds at any molar ratio of the cyclohexanone compound of the general formula (3) and the benzaldehyde compound of the general formula (4). However, the amount of the benzaldehyde compound of the general formula (4) is, for example, ordinarily 0.1 to 10.0 moles, preferably 0.33 to 3.0 moles per 1 mole of the cyclohexanone compound represented by the general formula (3).

Successively, description is made on the base used in the condensation reaction.

As specific examples of the base used in the condensation reaction, there can be mentioned inorganic bases including metal hydroxides (typified by sodium hydroxide, potassium hydroxide, etc.), metal carbonates (typified by sodium carbonate and potassium carbonate), etc.; and organic bases such as amine (e.g. triethylamine or piperazine), metal alkoxide (typified by sodium methoxide) and the like. Use of inorganic base such as sodium hydroxide, potassium hydroxide, sodium carbonate, potassium carbonate or the like is preferred from the standpoints of availability, easiness of handling, reactivity, etc. Use of, in particular, metal hydroxide is preferred and use of sodium hydroxide is preferred particularly.

The amount of the base used in the reaction is, for example, ordinarily 0.01 to 5.0 moles, preferably 0.1 to 3.0 moles per 1 mole of the cyclohexanone compound represented by the general formula (3).

The condensation reaction can be conducted sufficiently in a solvent-free state but a solvent may be used. The solvent used in the reaction can be any solvent as long as it does not hinder the reaction. As examples thereof, there can be mentioned water; nitrites such as acetonitrile, propionitrile and the like; alcohols such as methanol, ethanol, ethylene glycol and the like; amides such as dimethylformamide, dimethylacetamide, N-methylpyrrolidone and the like; aprotic polar solvents such as tetramethylurea, hexamethylphosphoric triamide (HMPA), propylene carbonate and the like; aromatic hydrocarbons such as toluene, xylene, chlorobenzene and the like; halogenated aliphatic hydrocarbons such as dichloromethane, chloroform and the like; ether type solvents such as diethyl ether, tetrahydrofuran, dioxane and the like; and aliphatic hydrocarbons such as pentane, n-hexane and the like. Use of water or an alcohol is preferred from the standpoint of reactivity, and use of water is referred particularly. These solvents can be used singly or in admixture of any mixing proportions.

The amount of the solvent used may be any level as long as it allows for sufficient mixing of the reaction system. However, the amount is ordinarily 0.05 to 10 liters, preferably 0.5 to 2 liters per 1 mole of the cyclohexanone compound represented by the general formula (3).

The temperature of the condensation reaction can be, for example, 0° C. to the refluxing temperature of the solvent, preferably 0 to 100° C.

The time of the condensation reaction is not particularly restricted; however, it is preferably 1 to 100 hours from the standpoint of, for example, suppression of by-product formation.

EXAMPLES

Next, the process for production of the present compound is specifically described by way of Examples. However, the present invention is in no way restricted to these Examples.

Example 1

Production of 2-benzylidenecyclohexanone

In a 500-ml, four-necked flask equipped with a mechanical stirrer, a reflux condenser and a thermometer were placed 53 g (0.5 mole) of benzaldehyde, 147 g (1.5 moles) of cyclohexanone and then 500 ml of water slowly. Then, there was slowly added 16.0 g (0.1 mole) of a 25% aqueous sodium hydroxide solution. The mixture was stirred at 90° C. for 3.5 hours and then cooled to room temperature. Thereto was added 200 ml of toluene for phase separation. The toluene layer was washed with water and a saturated aqueous sodium chloride solution in this order and then dried over anhydrous sodium sulfate. The resulting toluene layer was subjected to vacuum distillation to remove toluene and the excessive (remaining) cyclohexanone to obtain 100 g of a yellow oil. The oil was subjected to vacuum distillation to obtain 66 g of yellow crystals. Boiling point: 126 to 130° C./53.32 Pa (0.4 mmHg) The purity of the intended product in the crystals was >99.9% as measured by gas chromatography. Yield: 71%

$^1$H-NMR (300 MHz, CDCl$_3$): δ7.50-7.29 (m, 6H), 2.84 (dt, j=6.6, 2.4 Hz, 2H), 2.54 (t, j=6.6 Hz, 2H), 1.97-1.89 (m, 2H), 1.80-1.71 (m, 2H), ppm $^{13}$C-NMR (300 MHz, CDCl$_3$): δ202.0, 136.9, 135.9, 135.8, 130.5, 128.7, 128.6, 40.6, 29.2, 24.1, 23.6 ppm IR (neat): 2942.8, 2867.6, 2250.5, 1675.8, 1592.9, 1490.7, 1446.4, 1317.1, 1257.4, 1203.4, 1143.6, 1068.4, 910.2, 821.5, 732.8 cm$^{-1}$

GCMS M$^+$: 186

Example 2

Production of 2-benzylphenol

In a 100-ml, four-necked flask equipped with a magnetic stirrer, a reflux condenser and a thermometer were placed 18.6 g (0.1 mole) of the 2-benzylidenecyclohexanone produced in Example 1 and 51.7 g (0.3 mole) of diethyl maleate in this order. The flask inside was purged with nitrogen. Thereto was added 1.9 g (10 wt. %, 0.89 mmole as palladium) of 5% palladium carbon (a product of Wako Pure Chemical Industries, Ltd.). The system was made vacuum using an aspirator and then returned to ordinary pressure using nitrogen; this operation was repeated three times. Then, the system was stirred at 185° C. for 3 hours and cooled to room temperature. 100 ml of toluene was added to the system. Filtration was conducted to remove the palladium carbon. The filtrate was extracted with 100 ml of a 10% aqueous sodium hydroxide solution, and this operation was repeated four times. The aqueous layer was washed with 30 ml of toluene. To the resulting aqueous layer was added 35% hydrochloric acid until the aqueous layer became acidic, after which the aqueous layer was extracted with 100 ml of toluene. The toluene layer was washed with water and a saturated aqueous sodium chloride solution in this order. The toluene layer was dried over anhydrous sodium sulfate and then subjected to vacuum distillation to remove toluene, to obtain 10.7 g of an oil. This oil was subjected to Kugel Rohr distillation to obtain 9.0 of a colorless oil. Yield: 49% The purity of the intended product in the oil was >99.9% as measured by gas chromatography.

$^1$H-NMR (300 MHz, CDCl$_3$): δ7.44-7.29 (m, 5H), 7.26-7.20 (m, 2H), 7.04-6.98 (m, 1H), 6.84-6.81 (m, 1H), 4.96 (br, 1H), 4.11 (s, 2H) ppm $^{13}$C-NMR (300 MHz, CDCl$_3$): δ154.0, 140.3, 131.3, 129.1, 129.0, 128.2, 127.5, 126.7, 121.4, 116.1, 36.6 ppm IR (neat): 3527.2, 3027.7, 2360.4, 1592.9, 1494.6, 1454.1, 1328.7, 1213.0, 1093.4, 910.2, 850.5, 754.0, 730.9, 698.1 cm$^{-1}$

GCMS M$^+$: 184

Example 3

Production of 2-benzylphenol

In a 100-ml, four-necked flask equipped with a magnetic stirrer, a reflux condenser and a thermometer were placed 18.6 g (0.1 mole) of the 2-benzylidenecyclohexanone produced in Example 1 and 40 ml of diphenyl ether in this order. The flask inside was purged with nitrogen. Thereto was added 1.9 g (10 wt. %, 0.89 mmole as palladium) of 5% palladium carbon (a product of Wako Pure Chemical Industries, Ltd.). The system was made vacuum using an aspirator and then was returned to ordinary pressure using nitrogen; this operation was repeated three times. Then, the system was stirred at 240 to 250° C. for 8 hours and cooled to room temperature. 50 ml of toluene was added to the system. Filtration was conducted to remove the palladium carbon. The filtrate was extracted with 50 ml of a 10% aqueous sodium hydroxide solution, and this operation was repeated twice. The aqueous layer was washed with 50 ml of toluene. To the resulting aqueous layer was added 35% hydrochloric acid until the aqueous layer became acidic, after which the aqueous layer was extracted with 50 ml of ethyl acetate twice. The ethyl acetate layer was washed with water and a saturated aqueous sodium chloride solution in this order. The ethyl acetate layer was dried over anhydrous sodium sulfate and then subjected to vacuum distillation to remove ethyl acetate, to obtain 17.8 g of an oil. Yield: 97% The purity of the intended product in the oil was 95% as measured by gas chromatography.

Example 4

Production of 2-(4-methylbenzylidene)cyclohexanone

In a 500-ml, four-necked flask equipped with a mechanical stirrer, a reflux condenser and a thermometer were placed 30 g (0.25 mole) of p-methylbenzaldehyde, 73.5 g (0.75 mole) of cyclohexanone and then 250 ml of water slowly. Then, there was slowly added 4.0 g (25 mmole) of a 25% aqueous sodium hydroxide solution. The mixture was stirred at 73° C. for 1 hour. There was further added 8.0 g (50 mmole) of a 25% aqueous sodium hydroxide solution slowly, followed by stirring for 6 hours. The mixture was cooled to room temperature. Thereto was added 200 ml of toluene for phase separation. The toluene layer was washed with water and a saturated aqueous sodium chloride solution in this order and then dried over anhydrous sodium sulfate. The resulting toluene layer was subjected to vacuum distillation to remove toluene and the excessive (remaining) cyclohexanone to obtain 58.6 g of a yellow oil. To the obtained crude oil was added 50 ml of n-hexane for recrystallization, to obtain 25 g of yellow crystals. Yield: 50% The purity of the intended product in the crystals was 96% as measured by high performance liquid chromatography.

GCMS M$^+$: 200

Example 5

Production of 2-(4-methylbenzyl)phenol

In a 100-ml, four-necked flask equipped with a magnetic stirrer, a reflux condenser and a thermometer were placed 20.0 g (0.1 mole) of the 2-(4-methylbenzylidene)cyclohexanone produced in Example 4 and 40 ml of diphenyl ether in this order. The flask inside was purged with nitrogen. Thereto was added 2.0 g (10 wt. %, 0.47 mmole as palladium) of 5% palladium carbon (containing 50% of water, a product of N.E. CHEMCAT CORPORATION, a standard product). The system was made vacuum using an aspirator and then returned to ordinary pressure using nitrogen; this operation was repeated three times. Then, the system was stirred at 170° C. for 1 hour while the moisture was discharged out of the system, and further was stirred at 210° C. for 2 hours. The system was cooled to room temperature. 200 ml of toluene was added to the system. Filtration was conducted to remove the palladium carbon. The filtrate was extracted with 100 ml of a 10% aqueous sodium hydroxide solution, and this operation was repeated twice. The aqueous layer was washed with 50 ml of toluene. To the resulting aqueous layer was added 35% hydrochloric acid until the aqueous layer became acidic, after which the aqueous layer was extracted with 150 ml of ethyl acetate. The ethyl acetate layer was washed with water and a saturated aqueous sodium chloride solution in this order. The ethyl acetate layer was dried over anhydrous sodium sulfate and then subjected to vacuum distillation to remove ethyl acetate, to obtain 11.6 g of brown crystals. Yield: 59% The purity of the intended product in the crystals was 91% as measured by gas chromatography.

$^1$H-NMR (300 MHz, CDCl$_3$): δ7.18-6.80 (m, 8H), 5.10 (Br, 1H), 4.02 (s, 2H), 2.38 (s, 3H) ppm $^{13}$C-NMR (300 MHz, CDCl$_3$): δ154.1, 136.1, 131.2, 129.9, 129.6, 128.9, 128.0, 127.6, 121.2, 116.0, 36.2, 21.3 ppm IR (neat): 3529.1, 3021.9, 2919.7, 1704.8, 1592.9, 1511.9, 1454.1, 1328.7, 1234.2, 1089.6, 1041.4, 914.1, 810.0, 754.0 cm$^{-1}$

GCMS M$^+$: 198

Example 6

Production of 2-(4-fluorobenzylidene)cyclohexanone

In a 500-ml, four-necked flask equipped with a mechanical stirrer, a reflux condenser and a thermometer were placed 31 g (0.25 mole) of p-fluorobenzaldehyde, 73.5 g (0.75 mole) of cyclohexanone and then 250 ml of water slowly. Then, there was slowly added 8.0 g (50 mmole) of a 25% aqueous sodium hydroxide solution. The mixture was stirred at 90 to 95° C. for 3 hours and then cooled to room temperature. Thereto was added 100 ml of toluene for phase separation. The toluene layer was washed with water and a saturated aqueous sodium chloride solution in this order and then dried over anhydrous sodium sulfate. The resulting toluene layer was subjected to vacuum distillation to remove toluene and the excessive (remaining) cyclohexanone to obtain 53.8 g of a yellow oil. Crude yield: 108% The purity of the intended product in the oil was 89% as measured by high performance liquid chromatography.

GCMS M$^+$: 204

Example 7

Production of 2-(4-fluorobenzyl)phenol

In a 100-ml, four-necked flask equipped with a magnetic stirrer, a reflux condenser and a thermometer were placed 22.6 g (0.1 mole, calculated based on a purity of 89%) of the 2-(4-fluorobenzylidene)cyclohexanone produced in Example 6 and 40 ml of diphenyl ether in this order. The flask inside was purged with nitrogen. Thereto was added 2.0 g (10 wt. %, 0.94 mmole as palladium) of 5% palladium carbon (a product of Wako Pure Chemical Industries, Ltd.). The system was made vacuum using an aspirator and then returned to ordinary pressure using nitrogen; this operation was repeated three times. Then, the system was stirred at 250° C. for 7 hours and cooled to room temperature. 100 ml of toluene was added to the system. Filtration was conducted to remove the palladium carbon. The filtrate was extracted with 100 ml of a 10% aqueous sodium hydroxide solution, and this operation was repeated twice. The aqueous layer was washed with 30 ml of toluene. To the resulting aqueous layer was added 35% hydrochloric acid until the aqueous layer became acidic, after which the aqueous layer was extracted with 100 ml of ethyl acetate. The ethyl acetate layer was washed with water and a saturated aqueous sodium chloride solution in this order. The ethyl acetate layer was dried over anhydrous sodium sulfate and then subjected to vacuum distillation to remove ethyl acetate, to obtain 14.8 g of a red oil. Yield: 73% The purity of the intended product in the oil was 77% as measured by gas chromatography.

$^1$H-NMR (300 MHz, CDCl$_3$): δ7.24-7.12 (m, 4H), 7.08-6.91 (m, 3H), 6.79 (d, j=7.8 Hz, 1H), 5.24 (br, 1H), 3.99 (s, 2H) ppm $^{13}$C-NMR (300 MHz, CDCl$_3$): δ153.8, 131.1, 130.4, 130.3, 128.2, 127.3, 121.3, 115.9, 115.7, 115.4, 35.6 ppm IR (neat): 3425.0, 3037.3, 2925.5, 1716.3, 1602.6, 1508.1, 1456.0, 1328.7, 1222.7, 1157.1, 1097.3, 912.2, 823.5, 754.0 cm$^{-1}$

GCMS M$^+$: 202

Example 8

Production of 2-(4-methoxybenzylidene)cyclohexanone

In a 1,000-ml, four-necked flask equipped with a mechanical stirrer, a reflux condenser and a thermometer were placed 68 g (0.5 mole) of p-anisaldehyde, 147 g (1.5 moles) of cyclohexanone and then 200 ml of water slowly. Thereto was slowly added, in a water bath, an aqueous solution obtained by diluting 80 g (0.5 mole) of a 25% aqueous sodium hydroxide solution, with 300 ml of water. The system was stirred at 65° C. for 48 hours and cooled to room temperature. To the system were added 400 ml of toluene and 100 ml of water for phase separation. The aqueous layer was re-extracted with 100 ml of toluene. The toluene layers were combined and washed with water and a saturated aqueous sodium chloride solution in this order. The resulting toluene layer was dried over anhydrous sodium sulfate and subjected to vacuum distillation to remove toluene and the excessive (remaining) cyclohexanone. To the crude oil obtained were added 80 ml of toluene and 80 ml of n-hexane for recrystallization, to obtain 80.4 g of yellow crystals. Yield: 74% The purity of the intended product in the crystals was 88% as measured by high performance liquid chromatography.

GCMS M$^+$: 216

Example 9

Production of 2-(4-methoxybenzyl)phenol

In a 100-ml, four-necked flask equipped with a mechanical stirrer, a reflux condenser and a thermometer were placed 21.6 g (0.1 mole) of the 2-(4-methoxybenzylidene)cyclohexanone produced in Example 8 and 51.7 g (0.3 mole) of diethyl maleate in this order. The flask inside was purged with nitrogen. Thereto was added 2.2 g (10 wt. %, 1.0 mmole as palladium) of 5% palladium carbon (a product of Wako Pure Chemical Industries, Ltd.). The mixture was stirred at 180° C. for 6 hours and cooled to room temperature. 200 ml of toluene was added to the system. Filtration was conducted to remove the palladium carbon. The filtrate was extracted with 150 ml of a 7% aqueous sodium hydroxide solution, and this operation was repeated twice. The aqueous layer was washed with 50 ml of toluene. To the resulting aqueous layer was added 35% hydrochloric acid until the aqueous layer became acidic, after which the aqueous layer was extracted with 150 ml of ethyl acetate. The ethyl acetate layer was washed with water and a saturated aqueous sodium chloride solution in this order. The ethyl acetate layer was dried over anhydrous sodium sulfate and then subjected to vacuum distillation to remove ethyl acetate, to obtain 13.3 g of light yellow crystals. Yield: 62% The purity of the intended product in the crystals was 97% as measured by high performance liquid chromatography.

$^1$H-NMR (300 MHz, CDCl$_3$): δ7.14-7.07 (m, 4H), 6.89-6.71 (m, 4H), 5.02 (Br, 1H), 3.91 (s, 2H), 3.74 (s, 2H), ppm $^{13}$C-NMR (300 MHz, CDCl$_3$): δ158.3, 154.0, 132.2, 131.1, 130.0, 128.0, 127.7, 121.2, 116.0, 114.4, 55.6, 35.7 ppm IR (neat): 3351.7, 2991.1, 2917.8, 1592.9, 1508.1, 1454.1, 1357.6, 1238.1, 1180.2, 1027.9, 811.9, 759.8, 678.8 cm$^{-1}$

GCMS M$^+$: 214

Example 10

Production of 2-benzylidene-4-methylcyclohexanone

In a 500-ml, four-necked flask equipped with a mechanical stirrer, a reflux condenser and a thermometer were placed 10.6 g (0.1 mole) of benzaldehyde, 33.7 g (0.3 mole) of 4-methylcyclohexanone and then 100 ml of water slowly. Then, there was slowly added 3.2 g (20 mmole) of a 25% aqueous sodium hydroxide solution. The mixture was stirred at 97° C. for 4 hours and then cooled to room temperature. Thereto was added 50 ml of toluene for phase separation. The toluene layer was washed with water and a saturated aqueous sodium chloride solution in this order and then dried over anhydrous sodium sulfate. The resulting toluene layer was subjected to vacuum distillation to remove toluene and the excessive (remaining) 4-methylcyclohexanone to obtain 20 g of a yellow solid. Crude yield: 101% The purity of the intended product in the solid was 97% as measured by gas chromatography.

GCMS M$^+$: 198

Example 11

Production of 2-benzyl-4-methylphenol

In a 100-ml, four-necked flask equipped with a magnetic stirrer, a reflux condenser and a thermometer were placed 20.0 g (0.1 mole) of the 2-benzylidene-4-methylcyclohexanone produced in Example 10 and 51.7 g (0.3 mole) of diethyl maleate in this order. The flask inside was purged with nitrogen. Thereto was added 1.0 g (5 wt. %, 0.47 mmole as palladium) of 5% palladium carbon (a product of Wako Pure Chemical Industries, Ltd.). The system was made vacuum using an aspirator and then returned to ordinary pressure using nitrogen; this operation was repeated three times. Then, the system was stirred at 180° C. for 2 hours and at 200° C. for 2 hours, and then cooled to room temperature. 100 ml of toluene was added to the system. Filtration was conducted to remove the palladium carbon. The filtrate was subjected to vacuum distillation to remove the solvent including toluene and diethyl maleate. To the residue was added 100 ml of toluene, followed by extraction with 100 ml of a 10% aqueous sodium hydroxide solution; and this operation was repeated twice. To the aqueous layer was added 35% hydrochloric acid until the aqueous layer became acidic, after which the aqueous layer was extracted with 100 ml of ethyl acetate. The ethyl acetate layer was washed with water and a saturated aqueous sodium chloride solution in this order. The ethyl acetate layer was dried over anhydrous sodium sulfate and then subjected to vacuum distillation to remove ethyl acetate, to obtain 9.8 g of a brown oil. Yield: 50% The purity of the intended product in the oil was 91% as measured by gas chromatography.

¹H-NMR (300 MHz, CDCl₃): δ7.31-7.20 (m, 5H), 6.93-6.91 (m, 2H), 6.70-6.67 (m, 1H), 4.50 (br, 1H), 3.95 (s, 2H), 2.25 (s, 3H) ppm
¹³C-NMR (300 MHz, CDCl₃): δ151.7, 140.3, 131.8, 130.4, 128.91, 128.87, 128.4, 127.0, 126.5, 115.8, 36.6, 20.8 ppm
IR (neat): 3536.8, 3025.8, 2919.7, 1704.8, 1600.6, 1508.1, 1452.1, 1324.9, 1259.3, 1187.9, 1103.1, 811.9, 729.0, 698.1 cm⁻¹
GCMS M⁺: 198

Example 12

Production of 2-(4-chlorobenzylidene)cyclohexanone

In a 100-ml, four-necked flask equipped with a mechanical stirrer, a reflux condenser and a thermometer were placed 7.3 g (52 mmole) of p-chlorobenzaldehyde, 15.3 g (156 mmole) of cyclohexanone and then 50 ml of water slowly. Then, there was slowly added 1.6 g (10 mmole) of a 25% aqueous sodium hydroxide solution. The mixture was stirred at 90 to 95° C. for 5 hours and then cooled to room temperature. Thereto were added 50 ml of water and 30 ml of a saturated aqueous sodium chloride solution. The mixture was extracted with 50 ml of toluene twice. The toluene layer was washed with a saturated aqueous sodium chloride solution and then dried over anhydrous sodium sulfate. The resulting toluene layer was subjected to vacuum distillation to remove toluene and the excessive (remaining) cyclohexanone to obtain 11.5 g of a yellow oil. The oil was subjected to recrystallization from 20 ml of n-hexane to obtain 10.1 g of yellow crystals. The purity of the intended product in the crystals was 97% as measured by high performance liquid chromatography. Yield: 88%

¹H-NMR (300 MHz, CDCl₃): δ7.44-7.24 (m, 5H), 2.80 (dt, j=6.6, 2.1 Hz, 2H), 2.54 (t, j=6.6 Hz, 2H), 1.96-1.92 (m, 2H), 1.80-1.76 (m, 2H) ppm
¹³C-NMR (300 MHz, CDCl₃): δ201.7, 137.3, 134.6, 134.4, 134.2, 131.7, 128.8, 40.5, 29.1, 24.0, 23.5 ppm
IR (neat): 2940.9, 2865.7, 1677.8, 1589.1, 1488.8, 1402.0, 1319.1, 1255.4, 1143.6, 1093.4, 1010.5, 927.6, 835.0, 732.8 cm⁻¹
GCMS M⁺: 220

Example 13

Production of 2-(4-chlorobenzyl)phenol

In a 50-ml, eggplant-shaped flask equipped with a magnetic stirrer and a reflux condenser were placed 6.6 g (30 mmole) of the 2-(4-chlorobenzylidene)cyclohexanone obtained in Example 12, 1.44 g (45 mmole) of sulfur and 12 ml of 3,4-dichlorotoluene in this order. The system was made vacuum using an aspirator and then returned to ordinary pressure using nitrogen; and this operation was repeated three times. The system was stirred for 4 hours at a bath temperature of 200° C. and then cooled to room temperature. 50 ml of toluene was added to the system, followed by extraction with 50 ml of a 10% aqueous sodium hydroxide solution; and this operation was repeated twice. The aqueous layer was washed with 50 ml of toluene. Then, 35% hydrochloric acid was added to the aqueous layer until the aqueous layer became acidic, followed by extraction with 50 ml of ethyl acetate. The ethyl acetate layer was washed with a saturated aqueous sodium chloride solution, dried over anhydrous sodium sulfate, and then subjected to vacuum distillation to remove ethyl acetate, to obtain 1.5 g of a brown oil. The oil was subjected to Kugel Rohr distillation to obtain 0.6 g of light yellow crystals. Yield: 9% The purity of the intended product in the crystal was 97.8% as measured by high performance liquid chromatography.

¹H-NMR (300 MHz, CDCl₃): δ7.27-7.23 (m, 3H), 7.18-7.08 (m, 3H), 6.92-6.76 (m, 2H), 4.66 (br, 1H), 3.96 (s, 2H) ppm
¹³C-NMR (300 MHz, CDCl₃): δ153.9, 139.1, 132.1, 131.1, 130.4, 128.8, 128.2, 127.1, 121.2, 115.9, 35.7 ppm
IR (neat): 3504.0, 2919.7, 1589.1, 1490.7, 1452.1, 1328.7, 1259.3, 1218.8, 1162.9, 1087.7, 796.5, 763.7, 730.9 cm¹
GCMS M⁺: 218

The invention claimed is:

1. A process for producing a 2-benzylphenol compound represented by the following formula (2):

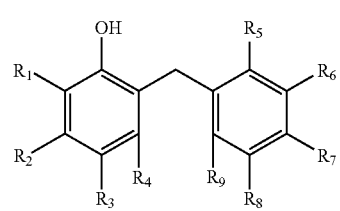

(2)

wherein, $R_1$, $R_2$, $R_3$ and $R_4$ are the same or different and are each independently hydrogen atom, substituted or unsubstituted alkyl group, substituted or unsubstituted cyclic alkyl group, trialkylsilyl group, alkoxy group, trialkylsilyloxy group, hydroxyalkyl group, alkoxyalkyl group, carboxyl group or metal salt thereof, alkoxycarbonyl group, amino group, alkylamino group, alkylcarbonylamino group, nitro group, substituted or unsubstituted phenyl group, substituted or unsubstituted phenoxy group, or substituted or unsubstituted heteroaryl group; or two of $R_1$, $R_2$, $R_3$ and $R_4$ are bonded with each other to form a ring; $R_5$, $R_6$, $R_7$, $R_8$ and $R_9$ are the same or different and are each independently hydrogen atom, substituted or unsubstituted alkyl group, substituted or unsubstituted cyclic alkyl group, substituted or unsubstituted alkenyl group, substituted or unsubstituted cyclic alkenyl group, substituted or unsubstituted alkynyl group, cyclic alkynyl group, trialkylsilyl group, hydroxyl group, alkoxy group, trialkylsilyloxy group, hydroxyalkyl group, alkoxyalkyl group, carboxyl group or metal salt thereof, alkoxycarbonyl group, amino group, alkylamino group, alkylcarbonylamino group, halogen atom, nitro group, substituted or unsubstituted phenyl group, substituted or unsubstituted phenoxy group, or substituted or unsubstituted heteroaryl group; or two of $R_5$, $R_6$, $R_7$, $R_8$ and $R_9$ may be bonded with each other to form a ring, the process comprising:

reacting, in the presence of a dehydrogenating agent, a benzylidenecyclohexanone compound represented by the following formula (1):

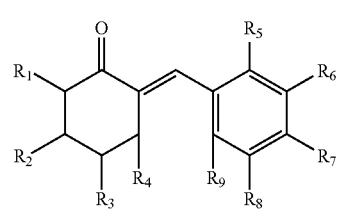

(1)

wherein, $R_1$, $R_2$, $R_3$, $R_4$, $R_5$, $R_6$, $R_7$, $R_8$ and $R_9$ have the same definitions as given above.

2. A process for producing a 2-benzylphenol compound represented by the following formula (2):

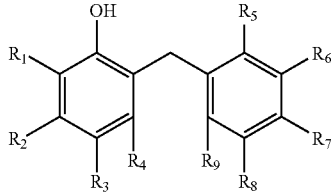

(2)

wherein, $R_1$, $R_2$, $R_3$ and $R_4$ are the same or different and are each independently hydrogen atom, substituted or unsubstituted alkyl group, substituted or unsubstituted cyclic alkyl group, trialkylsilyl group, alkoxy group, trialkylsilyloxy group, hydroxyalkyl group, alkoxyalkyl group, carboxyl group or metal salt thereof, alkoxycarbonyl group, amino group, alkylamino group, alkylcarbonylamino group, nitro group, substituted or unsubstituted phenyl group, substituted or unsubstituted phenoxy group, or substituted or unsubstituted heteroaryl group; or two of $R_1$, $R_2$, $R_3$ and $R_4$ are bonded with each other to form a ring; $R_5$, $R_6$, $R_7$, $R_8$ and $R_9$ are the same or different and are each independently hydrogen atom, substituted or unsubstituted alkyl group, substituted or unsubstituted cyclic alkyl group, substituted or unsubstituted alkenyl group, substituted or unsubstituted cyclic alkenyl group, substituted or unsubstituted alkynyl group, cyclic alkynyl group, trialkylsilyl group, hydroxyl group, alkoxy group, trialkylsilyloxy group, hydroxyalkyl group, alkoxyalkyl group, carboxyl group or metal salt thereof, alkoxycarbonyl group, amino group, alkylamino group, alkylcarbonylamino group, halogen atom, nitro group, substituted or unsubstituted phenyl group, substituted or unsubstituted phenoxy group, or substituted or unsubstituted heteroaryl group; or two of $R_5$, $R_6$, $R_7$, $R_8$ and $R_9$ may be bonded with each other to form a ring, by subjecting to a condensation reaction in the presence of a base, a cyclohexanone compound represented by the following formula (3):

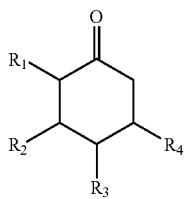

(3)

wherein, $R_1$, $R_2$, $R_3$ and $R_4$ have the same definitions as given above and a benzaldehyde compound represented by the following formula (4):

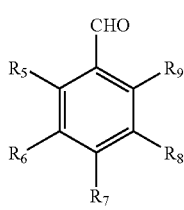

(4)

wherein, $R_5$, $R_6$, $R_7$, $R_8$ and $R_9$ have the same definitions as given above to obtain a benzylidenecyclohexanone compound represented by the following formula (1):

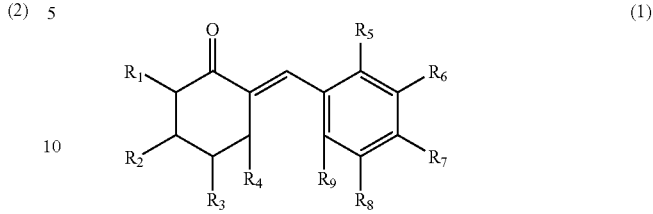

(1)

wherein, $R_1$, $R_2$, $R_3$, $R_4$, $R_5$, $R_6$, $R_7$, $R_8$ and $R_9$ have the same definitions as given above, and
then reacting the benzylidenecyclohexanone compound in the presence of a dehydrogenating agent.

3. A process for producing a 2-benzylphenol compound according to claim 2, wherein the dehydrogenating agent is a palladium catalyst or sulfur.

4. A process for producing a 2-benzylphenol compound according to claim 2, wherein the dehydrogenating agent is a palladium catalyst.

5. A process for producing a 2-benzylphenol compound according to claim 2, wherein the reaction of the benzylidenecyclohexanone compound represented by the formula (1) is conducted in a temperature range of 150 to 280° C.

6. A process for producing a 2-benzylphenol compound according to claim 2, wherein the reaction of the benzylidenecyclohexanone compound represented by the formula (1) is conducted in the presence of a hydrogen acceptor.

7. A process for producing a 2-benzylphenol compound according to claim 2, wherein the reaction of the benzylidenecyclohexanone compound represented by the formula (1) is conducted in the presence of an olefin.

8. A process for producing a 2-benzylphenol compound according to claim 7, wherein the reaction of the benzylidenecyclohexanone compound represented by the general formula (1) is conducted in a temperature range of 150 to 230° C.

9. A process for producing a 2-benzylphenol compound according to claim 6, wherein the reaction of the benzylidenecyclohexanone compound represented by the general formula (1) is conducted in a temperature range of 150 to 230° C.

10. A process for producing a 2-benzylphenol compound according to claim 1 or 2, wherein the dehydrogenating agent is sulfur.

11. A process for producing a 2-benzylphenol compound according to claim 2, wherein the reaction of the benzylidenecyclohexanone compound represented by the formula (1) is conducted in a temperature range of 180 to 250° C.

12. A process for producing a 2-benzylphenol compound according to claim 2, wherein the benzylidenecyclohexanone compound represented by the formula (1) is 2-benzylidenecyclohexanone, 2-(4-methylbenz-ylidene)cyclohexanone, 2-(4-methoxybenzylidene)cyclohexanone, 2-(4-chlorobenzylidene)cyclohexanone, 2-(4-fluorobenzylidene) cyclohexanone, 2(4-methylbenzylidene)-4-methylcyclohexanone, 2-(4-methoxybenzylidene)-4-methylcyclohexanone, 2-(4-chlorobenzylidene)-4-methylcyclohexanone, 2-(4-fluoro-benzylidene)-4-methylcyclohexanone, 2-(4-methylbenzylidene)-4-chlorocyclohexanone, 2-(4-methoxybenzylidene)-4-chlorocyclohexanone, 2-(4-chlorobenzylidene)-4-chlorocyclohexanone, 2-(4-fluorobenzylidene)-4-chlorocyclohexanone, 2-(4-methylbenzylidene)-4- fluorocyclohexanone,2-(4-methoxybenzylidene)-4-fluorocyclohexanone, 2-(4-chlorobenzylidene)-4-fluorocyclohexanone or 2-(4-fluorobenzylidene)-4-fluoromethylcyclohexanone.

13. A process for producing a 2-benzylphenol compound according to claim 2, wherein the cyclohexanone compound represented by the formula (3) is cyclohexanone or 4-methylcyclohexanone.

14. A process for producing a 2-benzylphenol compound according to claim 2, wherein the benzaldehyde compound represented by the formula (4) is benzaldehyde, 4-methylbenzaldehyde, 4-methoxybenzaldehyde, 4-chlorobenzaldehyde or 4-fluorobenzaldehyde.

15. A process for producing a 2-benzylphenol compound according to claim 1, wherein the dehydrogenating agent is a palladium catalyst or sulfur.

16. A process for producing a 2-benzylphenol compound according to claim 1, wherein the dehydrogenating agent is a palladium catalyst.

17. A process for producing a 2-benzylphenol compound according to claim 1, wherein the reaction of the benzylidenecyclohexanone compound represented by the formula (1) is conducted in a temperature range of 150 to 280° C.

18. A process for producing a 2-benzylphenol compound according to claim 1, wherein the reaction of the benzylidenecyclohexanone compound represented by the formula (1) is conducted in the presence of a hydrogen acceptor.

19. A process for producing a 2-benzylphenol compound according to claim 1, wherein the reaction of the benzylidenecyclohexanone compound represented by the formula (1) is conducted in the presence of an olefin.

20. A process for producing a 2-benzylphenol compound according to claim 1 wherein the reaction of the benzylidenecyclohexanone compound represented by the formula (1) is conducted in a temperature range of 180 to 250° C.

* * * * *